US006264957B1

(12) United States Patent
Collins

(10) Patent No.: US 6,264,957 B1
(45) Date of Patent: Jul. 24, 2001

(54) PRODUCT OF INFECTIOUS RESPIRATORY SYNCYTIAL VIRUS FROM CLONED NUCLEOTIDE SEQUENCES

(75) Inventor: Peter L. Collins, Rockville, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 08/720,132

(22) Filed: Sep. 27, 1996

Related U.S. Application Data

(60) Provisional application No. 60/007,083, filed on Sep. 27, 1995.

(51) Int. Cl.$^7$ .................................................. A61K 39/155
(52) U.S. Cl. ................................... 424/211.1; 435/235.1; 435/69.1; 435/69.7; 435/236; 435/325; 435/320.1
(58) Field of Search ........................... 435/91.32, 91.33, 435/172.3, 235.1, 325, 236, 237, 238, 239; 424/186.1, 211.1, 205.1; 536/23.72

(56) References Cited

U.S. PATENT DOCUMENTS

| 5,716,821 | * | 2/1998 | Wertz et al. ................. 435/235.1 |
| 5,789,229 |   | 8/1998 | Wertz et al. ................. 435/235.1 |

FOREIGN PATENT DOCUMENTS

| 92 01471 | 2/1992 | (WO). |
| 92 07940 | 5/1992 | (WO). |
| 92 21310 | 10/1993 | (WO). |
| 94 08022 | 4/1994 | (WO). |
| WO 97/06270 | 2/1997 | (WO). |

OTHER PUBLICATIONS

Schnell et al., 1994, "Infectious rabies viruses from cloned cDNA", EMBO J. 13:4195–4203.*
Whelan et al., 1995, "Efficient recovery of infectious vesicular stomatits virus entirely from cDNA clones", Proc. Natl. Acad. Sci. USA 92:8388–8392.*
Conzelmann et al., 1994, "Rescue of synthetic genomic RNA analogs of rabies virus by plasmid–encoded proteins", J. Virol. 68:713–719.*
Lawson et al., 1995, "Recombinant vesicular stomatitis virus from DNA", Proc. Natl. Acad. Sci. USA 92:4477–4481.*
Mink et al., 1991, "Nucleotide sequences of the 3' leader and 5' trailer regions of human respiratory syncytial virus genomic RNA", Virol. 185:615–624.*
Collins et al., 1991, "Rescue of synthetic analogs of respiratory syncytial virus genomic RNA and effect of truncations and mutations on the expression of a foreign reporter gene", Proc. Natl. Acad. Sci. USA 88:9663–9667.*

Collins et al., 1993, "Rescue of a 7502–nucleotide (49.3% of full–length) synthetic analog of respiratory syncytial virus genomic RNA", Virol. 195:252–256.*
Pastey et al., 1995, "Nucleotide sequence analysis of the non–structural NS1 (1C) and NS2 (1B) protein genes of bovine respiratory syncytial virus" Virol. 76:193–197.*
Pastey et al., 1993, "Structure and sequence comparison of bovine respiratory syncytial virus fusion protein", Virus Res. 29:195–202.*
Mink, M. A., et al., "Nucleotide sequences of the 3' leader and 5' trailer regions of human respiratory syncytial virus genomic RNA", Virology 185:615–624, 1991.*
McIntosh et al., Respiratory Syncytial Virus, in Virology, Second Edition, Fields et al., eds., Raven Press, Ltd., New York, pp. 1046 and 1047, 1990.*
Bukreyev, et al., "Recovery of Infectious Respiratory Syncytial Virus Expressing an Additional Foreign Gene," J. Virol., 70:6634–6641 (Oct., 1996).
Collins et al., "Rescue of Synthetic Analogs of Respiratory Syncytial Virus Genomic RNA and Effect of Truncations and Mutations on the Expression of a Foreign Reporter Gene," Proc. Natl. Acad. Sci. USA, 88:9663–9667 (Nov., 1991).
Collins et al., "Production of Infectious Human Respiratory Syncytial Virus from Cloned cDNA confirms an Essential Role for the Transcription Elongation Factor from the 5' Proximal Open Reading Frame of the M2 mRNA in Gene Expression and Provides a Capability for Vaccine Development," Proc. Natl. Acad. Sci. USA, 92:11563–11567 (Dec. 5, 1995).
Grosfeld et al., "RNA Replication by Respiratory Syncytial Virus (RSV) is Directed by the N, P, and L Proteins; Transcription also Occurs Under these Conditions but Requires RSV Superinfection for Efficient Synthesis of Full–Length mRNA," J. Virol., 69:5685 (Sep., 1995).
Kuo et al., "Effect of Mutations in the Gene–Start and Gene–End Sequence Motifs on Transcription of Monocistronic and Dicistronic Minigenomes of Respiratory Syncytial Virus," J. Virol., 70:6892–6901 (Oct., 1996).
Schnell et al., "Infectious Rabies Viruses from Cloned cDNA," EMBO J., 13:4195–4203 (1994).

* cited by examiner

*Primary Examiner*—Laurie Scheiner
*Assistant Examiner*—Jeffrey S. Parkin
(74) *Attorney, Agent, or Firm*—Townsend and Townsend and Crew LLP

(57) ABSTRACT

Isolated polynucleotide molecules provide RSV genome and antigenomes, including that of human, bovine or murine RSV or RSV-like viruses, and chimera thereof. The recombinant genome or antigenome can be expressed with a nucleocapsid (N) protein, a nucleocapsid phosphoprotein (P), a large (L) polymerase protein, and an RNA polymerase elongation factor to produce isolated infectious RSV particles. The recombinant RSV genome and antigenome can be modified to produce desired phenotypic changes, such as attenuated viruses for vaccine use.

22 Claims, 3 Drawing Sheets

US 6,264,957 B1

PRODUCT OF INFECTIOUS RESPIRATORY SYNCYTIAL VIRUS FROM CLONED NUCLEOTIDE SEQUENCES

This appln claims benefit of Provisional No. 60/007,083 filed Sep. 27, 1995.

BACKGROUND OF THE INVENTION

Human respiratory syncytial virus (RSV) is the most important pediatric respiratory pathogen worldwide. This ubiquitous, highly infectious agent emerges each year in seasonal epidemics. Nearly everyone is infected at least once within the first two years of life. RSV disease is responsible for considerable morbidity and mortality, especially in the very young; in the United States it causes an estimated 91,000 hospitalizations and 4500 deaths annually, and its impact is much greater in less affluent countries. RSV also has come to be recognized as an important agent of disease of immunocompromised adults and of the elderly.

Resistance to RSV reinfection induced by natural infection is incomplete but increases incrementally with repeated exposure. Thus, RSV can infect multiple times during childhood and life, but serious disease usually is limited to the first and sometimes second infections of life. The minimum goal of RSV immunoprophylaxis is to induce sufficient resistance to prevent serious disease associated with the initial infections.

A number of attenuated RSV strains were developed and evaluated as vaccines during the 1960's and 70's, but they were found to be either over- or under-attenuated, and in some cases exhibited genetic instability, as is common for single-stranded RNA viruses. Current strategies under investigation for RSV vaccine development are principally the parenteral administration of purified viral antigen or the development of live attenuated RSV for intranasal administration. The intranasal route provides direct stimulation of local immunity. It also partially abrogates the immunosuppressive effects of RSV-specific maternally derived serum antibodies, which typically are found in the very young. The parenteral administration of inactivated RSV or purified RSV antigen in experimental animals appears to be associated with enhanced immunopathology upon subsequent virus challenge, similar to the enhanced RSV disease associated with a formalin-inactivated vaccine evaluated in the 1960's. But this effect has never been observed with RSV infection of the respiratory tract, suggesting that live attenuated viruses have an important advantage in safety. To date, however, there is no approved vaccine or highly effective antiviral therapy for RSV.

Research efforts to produce a suitable RSV vaccine are impeded by poor viral growth in tissue culture, a lengthy replication cycle, virion instability, a negative-sense RNA genome, and a complex genome organization and gene products. RSV is a member of the pneumovirus genus of the paramyxovirus family, and its genome of single-stranded negative-sense RNA of 15,222 nucleotides has been sequenced completely for wild-type strain A2 virus as well as for an attenuated derivative thereof.

Some aspects of RNA synthesis by RSV appear to follow the general pattern of nonsegmented negative strand viruses. The genome template is tightly encapsidated with the major nucleocapsid (N) protein and is associated with the phosphoprotein (P) and large (L) polymerase subunit protein. Transcription begins at the 3' extragenic leader region and proceeds along the entire length by a sequential, stop-start mechanism guided by short template signals flanking the genes. This yields at least ten major species of mRNA which encode at least ten major proteins. RNA replication occurs by a switch to the synthesis of a full length positive-sense "antigenome" which also is tightly encapsidated and serves as the template for the synthesis of progeny genome.

The viral genomic RNA of negative-strand viruses is not infectious alone as free RNA. In virions or intracellularly, viral RNA is always found tightly encapsidated in a ribonucleoprotein core. This nucleocapsid contains the viral proteins necessary for transcription and replication and has long been regarded as the minimum unit of infectivity (Brown et al., J. Virol. 1: 368–373 (1967)). Thus, it has been recognized that the generation of biologically active synthetic viral RNA from cDNA will require complementation by viral protein, leading to the assembly of functional nucleocapsids (Collins et al., Proc. Natl. Acad. Sci. USA 88: 9663–9667 (1991), and Collins et al., Virology 195: 252–256 (1993)). The ability to produce live RSV from cDNA is of particular importance because it would permit the introduction of specific engineered changes, including attenuating mutations, into the genome of infectious virus in an effort to produce safe and effective RSV vaccines.

Short, internally-deleted analogs of genome or antigenome RNA ("minigenomes") have been shown to participate in transcription and replication when synthesized intracellularly in the presence of the appropriate viral proteins. For two rhabdoviruses, rabies and vesicular stomatitis viruses, infectious virus has been produced by coexpression of a complete cDNA-encoded antigenome RNA in the presence of the N, P and L proteins (Schnell et al., EMBO J. 13: 4195–4203 (1994) and Lawson et al., Proc. Natl. Acad. Sci. USA 92: 4477–4481 (1995)).

RSV possesses a number of properties which distinguishes it and other members of the genus Pneumovirus from the better characterized paramyxoviruses of the genera Paramyxovirus, Rubulavirus and Morbillivirus. These differences include a greater number of mRNAs, an unusual gene order at the 3' end of the genome, species-to-species variability in the order of the glycoprotein and M2 genes, a greater diversity in intergenic regions, an attachment protein that exhibits mucin-like characteristics, extensive strain-to-strain sequence diversity, and several proteins not found in any or most of the other nonsegmented negative strand RNA viruses.

RSV remains the most common cause of severe viral lower respiratory tract disease in infants and children. Consequently, an urgent need remains for the ability to engineer a safe and effective vaccine that is able to prevent the serious illness in this population that often requires hospitalization. Quite surprisingly, the present invention fulfills this and other related needs by providing methods for introducing defined, predetermined changes into infectious RSV.

SUMMARY OF THE INVENTION

The present invention provides an isolated infectious RSV particle which comprises a recombinant RSV genome or antigenome, a nucleocapsid (N) protein, a nucleocapsid phosphoprotein (P), a large (L) polymerase protein, and an RNA polymerase elongation factor. The RNA polymerase elongation factor can be M2(ORF1) of RSV. The isolated infectious RSV particle can be a viral or subviral particle. The isolated infectious RSV virus may be a human RSV, a bovine or murine RSV, or the genome or antigenome can be a chimera of two or more different RSV genomes, such as having nucleotide segments from human and bovine RSV.

In other embodiments the invention provides a method for producing an infectious RSV particle from one or more isolated polynucleotide molecules encoding an RSV. An expression vector which comprises an isolated polynucleotide molecule encoding a RSV genome or antigenome and an expression vector which comprises one or more isolated polynucleotide molecules that encodes N, P, L and RNA polymerase elongation factor proteins are coexpressed in a cell or cell-free lysate, thereby producing an infectious RSV particle. The RSV genome or antigenome and the N, P, L and RNA polymerase elongation factor proteins can be coexpressed by the same or different expression vectors. In some instances the N, P, L and RNA polymerase elongation factor proteins are each encoded on different expression vectors. The polynucleotide molecule encoding the RSV genome or antigenome is from a human, bovine or murine RSV sequence, and can be a chimera of a human RSV strain sequence and at least one non-human RSV sequence, or can encodes the genome or antigenome of a wild-type RSV strain. The RSV genome or antigenome can be modified from a wild-type RSV strain by a nucleotide insertion, rearrangement, deletion or substitution, so as to encode a phenotypic alteration such as one that results in attenuation, temperature-sensitivity, cold-adaptation, small plaque size, host range restriction, or a change in an immunogenic epitope of RSV. The polynucleotide can encode a genome or antigenome of a nonhuman RSV virus, or can be a chimera of a nonhuman RSV and at least one other RSV or human or nonhuman origin. The polynucleotide molecule encoding the genome or antigenome can also be modified to include a nucleotide sequence that encodes a cytokine, a T-helper epitope, a G protein of a different RSV subgroup, a restriction site marker, or a protein of a microbial pathogen (e.g., virus, bacterium or fungus) capable of eliciting a protective immune response in the intended host.

In other embodiments the invention provides a cell or cell-free lysate containing an expression vector which comprises an isolated polynucleotide molecule encoding a RSV genome or antigenome and an expression vector which comprises one or more isolated polynucleotide molecules that encodes N, P, L and RNA polymerase elongation factor proteins of RSV. Upon expression the genome or antigenome and N, P, L, and RNA polymerase elongation factor proteins combine to produce an infectious RSV particle, such as viral or subviral particle.

In another aspect the invention provides an isolated polynucleotide molecule which comprises an operably linked transcriptional promoter, a polynucleotide sequence encoding an RSV genome or antigenome, and a transcriptional terminator. The RSV genome or antigenome can be a human RSV sequence and modified versions thereof, such as that exemplified in SEQ ID NO:1 (which depicts the 5' to 3' positive-sense sequence whereas the genome itself is negative-sense). The polynucleotide can also encodes a genome or antigenome of a nonhuman RSV virus, or encode a chimera of a nonhuman RSV and at least one other RSV of human or nonhuman origin.

BRIEF DESCRIPTION OF THE DRAWINGS

FIG. 1A shows the structures of the cDNA and the encoded antigenome RNA (not to scale). The diagram of the antigenome includes the following features: the 5'-terminal nonviral G triplet contributed by the T7 promoter, the four sequence markers at positions 1099 (which adds one nt to the length), 1139, 5611, and 7559 (numbering referring to the first base of the new restriction site), the ribozyme and tandem T7 terminators, and the single nonviral 3'-phosphorylated U residue contributed to the 3' end by ribozyme cleavage (the site of cleavage is indicated with an arrow). Cloned cDNA segments representing in aggregate the complete antigenome are also shown. The box illustrates the removal of the BamHI site, a modification that facilitated assembly: the naturally occurring BamHI-SalI fragment (the BamHI site is shown in the top line in positive sense, underlined) was replaced with a PCR-generated BglII-SalI fragment (the BglII site is shown in the bottom line, underlined; its 4-nt sticky end [shown in italics] is compatible with that of BamHI). This resulted in a single nt change (middle line, underlined) which was silent at the amino acid level.

FIG. 1B shows the sequence markers contained in the cDNA-encoded antigenome RNA, where sequences are positive sense and numbered relative to the first nt of the leader region complement as 1; identities between strains A2 and 18537, representing subgroups A and B, respectively, are indicated with dots; sequences representing restriction sites in the cDNA are underlined; gene-start (GS) and gene-end (GE) transcription signals are boxed; the initiation codon of the N translational open reading frame at position 1141 is italicized, and the sequence markers are shown underneath each sequence. In the top sequence, a single C residue was inserted at position 1099 to create an AflII site in the NSII-N intergenic region, and the AG at positions 1139 and 1140 immediately upstream of the N translational open reading frame were replaced with CC to create a new NcoI site. In the middle sequence, substitution of G and U at positions 5612 and 5616, respectively, created a new StuI site in the G-F intergenic region. In the bottom sequence, a C replacement at position 7560 created a new SphI site in the F-M2 intergenic region.

DESCRIPTION OF THE SPECIFIC EMBODIMENTS

Figure 1A:
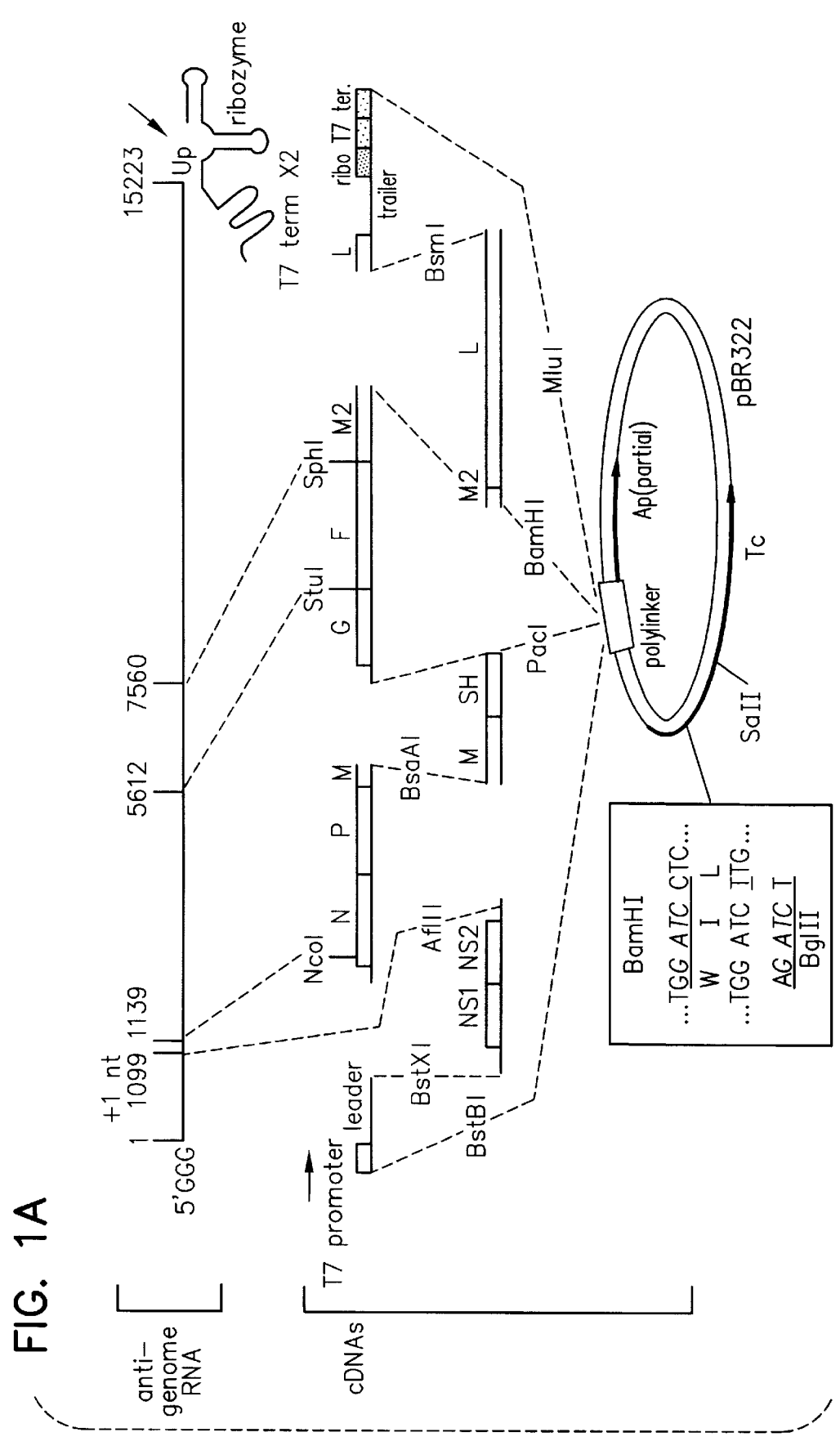
FIGS. 1A and 1B show the construction of cDNA encoding RSV antigenome RNA, where

The present invention provides the production of infectious RSV from cDNA. Infectious RSV is produced by the intracellular coexpression of a cDNA that encodes the RSV genome or antigenome RNA, together with those viral proteins necessary to generate a transcribing, replicating nucleocapsid, preferably one or more sequences that encode major nucleocapsid (N or NP) protein, nucleocapsid phosphoprotein (P), large (L) polymerase protein, and an M2(ORF1) protein. Infectious RSV particles are produced by the recombinant system. The recombinant production system permits the introduction of defined changes into infectious RSV, which changes are useful in a wide variety of applications such as: the development of live attenuated vaccine strains bearing predetermined, defined attenuating mutations; analysis of RSV molecular biology and pathogenesis using, e.g., defined mutations to alter functions or expression of RSV proteins; improvement in the growth in culture; identification of attenuating mutations in existing or future vaccine strains by distinguishing between silent incidental mutations versus those responsible for phenotype differences; production of modified vaccine virus to accommodate antigenic drift; enhancement of vaccine immunogenicity; ablation of epitopes associated with undesirable immunopathology; insertion of foreign genes, in whole or in part, encoding protective antigens to generate RSV strains capable of inducing immunity to both RSV and the virus or agent from which the protective antigen was derived; insertion of foreign genes, in whole or in part, encoding modulators of the immune system such as cytokines or T cell epitopes, to enhance the immunogenicity of the vaccine virus; etc.

According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodologic or other grounds.

A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (G), fusion (F), M2(ORF1), M2(ORF2), and L, substantially as described in Mink et al., *Virology* 185: 615–624 (1991), Stec et al., *Virology* 183: 273–287 (1991), and Connors et al., *Virol.* 208:478–484 (1995), incorporated herein by reference. For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by, e.g., assembling cloned cDNA segments, representing in aggregate the complete antigenome, by polymerase chain reaction (PCR; described in, e.g., U.S. Pat. Nos. 4,683,195 and 4,683,202, and *PCR Protocols: A Guide to Methods and Applications*, Innis et al., eds., Academic Press, San Diego (1990), incorporated herein by reference) of reverse-transcribed copies of RSV mRNA or genome RNA. For example, cDNAs containing the lefthand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoR1 fragment with a synthetic DNA containing convenient restriction enzyme sites. pBR322 stabilized nucleotides 3716–3732 of the RSV sequence, which otherwise sustained nucleotide deletions or insertions, and propagation of the plasmid was in bacterial strain DH10B to avoid an artifactual duplication and insertion which otherwise occurred in the vicinity of nt4499. For ease of preparation the G, F and M2 genes can be assembled in a separate vector, as are the L and trailer sequences. The righthand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al.,*J. Virol.* 69:5677–5686 (1995)), which would yield a 3' end containing a single nonviral nucleotide, or can any of the other suitable ribozymes such as that of hepatitis delta virus (Perrotta et al., *Nature* 350:434–436 (1991)) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example shown in FIG. 1A, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly-correct 3' end, the trailer end was constructed to be adjacent to a hammerhead ribozyme, which upon cleavage would donate a single 3'-phosphorylated U residue to the 3' end of the encoded RNA.

A variety of nucleotide insertions and deletions can be made in the RSV genome or antigenome. The nucleotide length of the genome of wild type human RSV (15,222 nucleotides) is a multiple of six, and members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsidating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding the genome or antigenome include by reverse transcription-PCR using improved PCR conditions (e.g., as described in Cheng et al., *Proc. Natl. Acad. Sci. USA* 91:5695–5699 (1994)), incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the larger size genome or antigenome.

By virtue of the present invention a variety of alterations in the RSV genome or antigenome for incorporation into infectious recombinant RSV are made possible. For example, foreign genes may be inserted, the order of genes changed, gene overlap removed, the RSV genome promoter replaced with its antigenome counterpart, portions of genes removed (e.g., the cytoplasmic tails of glycoprotein genes), and even entire genes deleted. Modifications in the sequence can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

The infectious RSV produced from cDNA-expressed genome or antigenome can be any of the RSV or RSV-like strains, e.g., human, bovine, murine, etc., or of any pneumovirus, e.g., pneumonia virus of mice or turkey rhinotracheitis virus. To engender a protective immune response, the RSV strain may be one which is endogenous to the subject being immunized, such as human RSV being used to immunize humans. The genome or antigenome can be modified, however, to express RSV genes from different types. Thus, infectious RSV intended for administration to humans may be human RSV that has been modified to contain genes from a bovine or murine RSV type such as for the purpose of attenuation, or a bovine RSV may be modified to contain genes that encode epitopes or proteins that elicit protection against human RSV infection, e.g., the human RSV glycoprotein genes can be substituted for the bovine glycoprotein genes such that the bovine RSV, which has a restricted ability to replicate in a human host, elicits a protective immune response in humans against human RSV strains.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection. The need for the M2(ORF1) protein is consistent with its role as a transcription elongation factor. The need for expression of the RNA polymerase elongation factor protein for negative strand RNA viruses is a feature of the present invention. M2(ORFl) can be supplied by expression of the complete M2-gene, although in this form the second ORF2 may also be expressed and have an inhibitory effect on RNA replication. Therefore, for production of infectious virus using the complete M2 gene the activities of the two ORFs should be balanced to permit sufficient expression of M(ORF1) to provide transcription elongation activity yet not so much of M(ORF2) to inhibit RNA replication. Alternatively, the ORF1 protein is provided from a cDNA engineered to lack ORF2 or which encodes a defective ORF2. Efficiency of virus production may also be improved by co-expression of additional viral protein genes, such as those encoding envelope constituents (i.e., SH, M, G, F proteins).

Isolated polynucleotides (e.g., cDNA) encoding the genome or antigenome and, separately, the N, P, L and M2(ORF1) proteins, are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14: 725 (1978); Corsaro and Pearson, *Somatic Cell Genetics* 7: 603 (1981); Graham and Van der Eb, *Virology* 52: 456 (1973)), electroporation (Neumann et al., *EMBO J.* 1: 841–845 (1982)), DEAE-dextran mediated transfection (Ausubel et al., (ed.) *Current Protocols in Molecular Biology*, John Wiley and Sons, Inc., New York (1987), incorporated herein by reference), cationic lipid-mediated transfection (Hawley-Nelson et al., *Focus* 15: 73–79 (1993)) or a commercially available transfection regent, e.g., LipofectACE® (Life Technologies). The N, P, L and M2(ORF1) proteins are encoded by one or more expression vectors which can be the same or separate from that which encodes the genome or antigenome, and various combinations thereof. Additional proteins may be included as desired, encoded on a its own vector or on a vector encoding a N, P, L, or M2(ORF1) protein or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology*, 210: 202–205 (1995), incorporated herein by reference). The viral proteins, and/or T7 RNA polymerase, can also be provided from transformed mammalian cells, or by transfection of preformed mRNA or protein.

Alternatively, synthesis of antigenome or genome together with the above-mentioned viral proteins can be done in vitro (cell-free) in a combined transcription-translation reaction, followed by transfection into cells. Or, antigenome or genome RNA can be synthesized in vitro and transfected into cells expressing RSV proteins.

Having the infectious clone of the invention permits the alteration of the RSV genome (or antigenome) by introducing defined mutations. By "infectious clone" is meant cDNA or its product, synthetic or otherwise, which can be transcribed into genomic or antigenomic RNA capable of serving as template to produce the genome of infectious virus or subviral particle. Defined mutations can be introduced by conventional techniques (e.g., site-directed mutagenesis)

into a cDNA copy of the genome or antigenome. The use of antigenome cDNA subfragments to assemble a complete antigenome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gen kit of Bio-Rad, or a method using the double-stranded plasmid directly as template such as the Chameleon mutagenesis kit of Stratagene, or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad Laboratories, Richmond, Calif. In brief, cDNA encoding an RSV genome or antigenome is cloned into the plasmid pTZ18U, and used to transform DH5α F' cells (Life Technologies Inc., Gaithersburg, Md.). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

The ability to introduce defined mutations into infectious RSV has many applications, including the analyses of RSV molecular biology and pathogenesis. For example, the functions of the RSV proteins, including the NS1, NS2, SH, M2(ORF1) and M2(ORF2) proteins, can be investigated by introducing mutations which ablate or reduce their level of expression, or which yield mutant protein.

As another example, the sequence at the cleavage site of the F protein, or the putative attachment domain of the G protein, can be modified to evaluate effects on growth in tissue culture and infection and pathogenesis in experimental animals.

The roles of various genome RNA structural features, such as promoters, intergenic regions, gene overlap, and transcription signals, can be evaluated using the methods and compositions of the present invention. Evaluation of trans-acting proteins and cis-acting RNA sequences using the complete antigenome cDNA can be conducted in parallel using RSV minigenomes (e.g., Grosfeld et al., *J. Virol.* 69: 5677–5686 (1995), incorporated herein by reference), whose helper-dependent status is useful in the characterization of those mutants which are too inhibitory to be recovered in replication-independent infectious virus.

A number of attenuated RSV strains as candidate vaccines for intranasal administration have been developed using multiple rounds of chemical mutagenesis to introduce multiple mutations into a virus which had already been attenuated during cold-passage (e.g., Connors et al., *Virology* 208: 478–484 (1995); Crowe et al., *Vaccine* 12: 691–699 (1994); and Crowe et al., *Vaccine* 12: 783–790 (1994), incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses indicates that each level of increased attenuation is associated with two or more new nucleotide and amino acid substitutions (Connors et al., supra). The present invention provides the ability to distinguish between silent incidental mutations versus those responsible for phenotype differences by introducing the mutations, separately and in various combinations, into the genome or antigenome of infectious wild-type RSV. This process identifies mutations responsible for phenotypes such as attenuation, temperature sensitivity, cold-adaptation, small plaque size, host range restriction, etc. Mutations from this menu can then be introduced in various combinations to calibrate a vaccine virus to an appropriate level of attenuation, etc., as desired. Moreover, the present invention provides the ability to combine mutations from different strains of virus into one strain.

The present invention also provides new methods of attenuation. For example, individual internal genes of human RSV can be replaced with their bovine, murine or other RSV counterpart. This may include part or all of one or more of the NS1, NS2, N, P, M, SH, M2(ORF1), M2(ORF2) and L genes, or non-immunogenic parts of the G and F genes. Reciprocally, means are provided to generate a live attenuated bovine RSV by inserting human attenuating genes into a bovine RSV genome or antigenome background. Human RSV bearing bovine RSV glycoproteins provides a host range restriction favorable for human vaccine preparations. Bovine RSV sequences which can be used in the present invention are described in, e.g., Pastey et al., *J. Gen. Viol.* 76:193–197 (1993); Pastey et al., *Virus Res.* 29:195–202 (1993); Zamora et al., *J. Gen. Virol.* 73:737–741 (1992); Mallipeddi et al., *J. Gen. Virol.* 74:2001–2004 (1993); Mallipeddi et al., *J. Gen. Virol.* 73:2441–2444 (1992); and Zamora et al., *Virus Res.* 24:115–121 (1992), each of which is incorporated herein by reference.

The invention also provides the ability to analyze other types of attenuating mutation and to incorporate them into infectious RSV for vaccine or other uses. For example, a tissue culture-adapted nonpathogenic strain of pneumonia virus of mice (the murine counterpart of RSV) lacks a cytoplasmic tail of the G protein (Randhawa et al., *Virology* 207: 240–245 (1995)). By analogy, the cytoplasmic and transmembrane domains of each of the RSV glycoproteins, F, G and SH, can be deleted or modified to achieve attenuation.

Other mutations for use in infectious RSV of the present invention include mutations in cis-acting signals identified during mutational analysis of RSV minigenomes. For example, insertional and deletional analysis of the leader and trailer and flanking sequences identified viral promoters and transcription signals and provided a series of mutations associated with varying degrees of reduction of RNA replication or transcription. Saturation mutagenesis (whereby each position in turn is modified to each of the nucleotide alternatives) of these cis-acting signals also has identified many mutations which reduced (or in one case increased) RNA replication or transcription. Any of these mutations can be inserted into the complete antigenome or genome as described herein. Other mutations involve replacement of the 3' end of genome with its counterpart from antigenome, which is associated with changes in RNA replication and transcription. In addition, the intergenic regions (Collins et al., *Proc. Natl. Acad. Sci. USA* 83:4594–4598 (1986), incorporated herein by reference) can be shortened or lengthened or changed in sequence content, and the naturally-occurring gene overlap (Collins et al., *Proc. Natl. Acad. Sci. USA* 84:5134–5138 (1987), incorporated herein by reference) can be removed or changed to a different intergenic region by the methods described herein.

In another embodiment, RSV useful in a vaccine formulation can be conveniently modified to accommodate antigenic drift in circulating virus. Typically the modification will be in the G and/or F proteins. The entire G or F gene, or the segment(s) encoding particular immunogenic regions thereof, is incorporated into the RSV genome or antigenome cDNA by replacement of the corresponding region in the infectious clone or by adding one or more copies of the gene such that several antigenic forms are represented. Progeny virus produced from the modified RSV cDNA are then used in vaccination protocols against the emerging strains. Further, inclusion of the G protein gene of RSV subgroup B would broaden the response to cover a wider spectrum of the relatively diverse subgroup A and B strains present in the human population.

An infectious RSV clone of the invention can also be engineered to enhance its immunogenicity and induce a level of protection greater than that provided by natural infection, or vice versa, to identify and ablate epitopes associated with undesirable immunopathologic reactions. Enhanced immunogenicity of the vaccines produced by the present invention addresses one of the greatest obstacles to controlling RSV, namely the incomplete nature of immunity induced by natural infection. An additional gene may be inserted into or proximate to the RSV genome or antigenome which is under the control of an independent set of transcription signals. Genes of interest include those encoding cytokines (e.g., IL-2 through IL-15, especially IL-3, IL-6 and IL-7, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

For vaccine use, virus produced according to the present invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, Mg$^{++}$ and HEPES, with or without adjuvant, as further described below.

Thus RSV vaccines of the invention contain as an active ingredient an immunogenetically effective amount of RSV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art.

Upon immunization with a RSV composition as described herein, via aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV infection, particularly of the lower respiratory tract.

The host to which the vaccine are administered can be any mammal which is susceptible to infection by RSV or a closely related virus and which host is capable of generating a protective immune response to the antigens of the vaccinizing strain. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the RSV of the invention are administered to a host susceptible to or otherwise at risk of RSV infection to enhance the host's own immune response capabilities. Such an amount is defined to be a "immunogenically effective dose." In this use, the precise amounts again depend on the host's state of health and weight, the mode of administration, the nature of the formulation, etc., but generally range from about $10^3$ to about $10^6$ plaque forming units (PFU) or more of virus per host, more commonly from about $10^4$ to $10^5$ PFU virus per host. In any event, the vaccine formulations should provide a quantity of modified RSV of the invention sufficient to effectively protect the host patient against serious or life-threatening RSV infection.

The RSV produced in accordance with the present invention can be combined with viruses of the other subgroup or strains to achieve protection against multiple RSV subgroups or strains, or protective epitopes of these strains can be engineered into one virus as described herein. Typically the different viruses will be in admixture and administered simultaneously, but may also be administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

In some instances it may be desirable to combine the RSV vaccines of the invention with vaccines which induce protective responses to other agents, particularly other childhood viruses. For example, the RSV vaccine of the present invention can be administered simultaneously with parainfluenza virus vaccine, such as described in Clements et al., *J. Clin. Microbiol.* 29:1175–1182 (1991), which is incorporated herein by reference. In another aspect of the invention the RSV can be employed as a vector for protective antigens of other respiratory tract pathogens, such as parainfluenza, by incorporating the sequences encoding those protective antigens into the RSV genome or antigenome which is used to produce infectious RSV as described herein.

Single or multiple administrations of the vaccine compositions of the invention can be carried out. In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection.

Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be advantageous for different recipient groups. For example, an engineered RSV strain expressing an additional protein rich in T cell epitopes may be particularly advantageous for adults rather than for infants.

In yet another aspect of the invention the RSV is employed as a vector for transient gene therapy of the respiratory tract. According to this embodiment the recombinant RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient. Administration is typically by aerosol, nebulizer, or other topical application to the respiratory tract of the patient being treated. Recombinant RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

Example I
Construction of cDNA Encoding RSV Antigenome

A cDNA clone encoding the antigenome of RSV strain A2 was constructed, as shown in FIG. 1A. The cDNA was synthesized in segments by reverse transcription (RT) and polymerase chain reaction (PCR) using synthetic oligonucleotides as primers and intracellular RSV mRNA or genome RNA isolated from purified virions as template. The final cDNA was flanked on the leader end by the promoter for T7 RNA polymerase, which included three transcribed G residues for optimal activity; transcription would result in the donation of these three nonviral G's to the 5' end of the antigenome. To generate a nearly-correct 3' end, the cDNA trailer end was constructed to be adjacent to a previously-described hammerhead ribozyme, which upon cleavage would donate a single 3'-phosphorylated U residue to the 3' end of the encoded RNA (Grosfeld et al., *J. Virol.* 69:5677–5686, incorporated herein by reference). The ribozyme sequence was followed by a tandem pair of terminators of T7 RNA polymerase. (The addition of three 5' G residues and one 3' U residue to a cDNA-encoded RSV minigenome containing the chloramphenicol acetyl transferase (CAT) reporter gene had no effect on the expression of CAT when complemented by RSV.)

FIG. 1A shows the structures of the cDNA and the encoded antigenome RNA (not to scale). The diagram of the antigenome (at top) includes the following features: the 5'-terminal nonviral G triplet contributed by the T7 promoter, the four sequence markers at positions 1099 (which adds one nt to the length), 1139, 5611, and 7559, the ribozyme and tandem T7 terminators, and the single nonviral 3'-phosphorylated U residue contributed to the 3' end by ribozyme cleavage (the site of cleavage is indicated with an arrow) (13).

Cloned cDNA segments (FIG. 1A, middle) representing in aggregate the complete antigenome were constructed by RT-PCR of RSV mRNA or genome RNA. cDNAs containing the lefthand end of the antigenome, spanning from the T7 promoter and leader region complement to the SH gene, were assembled in a version of pBR322 (FIG. 1A, bottom) in which the naturally-occurring BamHI site had been ablated by mutagenesis and the PstI-EcoRI fragment replaced with a synthetic polylinker containing unique restriction sites (including BstBI, BstXI, PacI, BamHI, MluI) designed to facilitate assembly. The box in FIG. 1A shows the removal of the BamHI site. The naturally occurring BamHI-SalI fragment (the BamHI site is shown in the top line in positive sense, underlined) was replaced with a PCR-generated BglII-SalI fragment (the BglII site is shown in the bottom line, underlined; its 4-nt sticky end [italics] is compatible with that of BamHI). This resulted in a single nt change (middle line, underlined) which was silent at the amino acid level. These modifications to the vector facilitated construction of the cDNA by rendering unique a BamHI site in the antigenome cDNA.

The G, F and M2 genes were assembled in a separate plasmid, as were the L, trailer and flanking ribozyme and tandem T7 transcription terminators. The G-to-M2 piece was then inserted into the PacI-BamHI window of the leader-to-SH plasmid. This in turn was the recipient for the L-trailer-ribozyme-terminator piece inserted into the BamHI to MluI, yielding the complete antigenome.

Four restriction site markers (FIG. 1B) were introduced into the antigenome CDNA by incorporating the changes into oligonucleotide primers used in RT-PCR. This was done to facilitate assembly, provide a means to identify recombinant virus, and illustrate the ability to introduce changes into infectious RSV. Three sites were in intergenic regions and the fourth in a nontranslated gene region, and they involved a total of five nt substitutions and a single nt insertion. This increased the length of the encoded antigenome by one nt from that of wild type to a total of 15,223 nt (SEQ ID NO:1, which depicts the 5' to 3' positive-sense sequence whereas the genome itself is negative-sense).

Figure 1B:
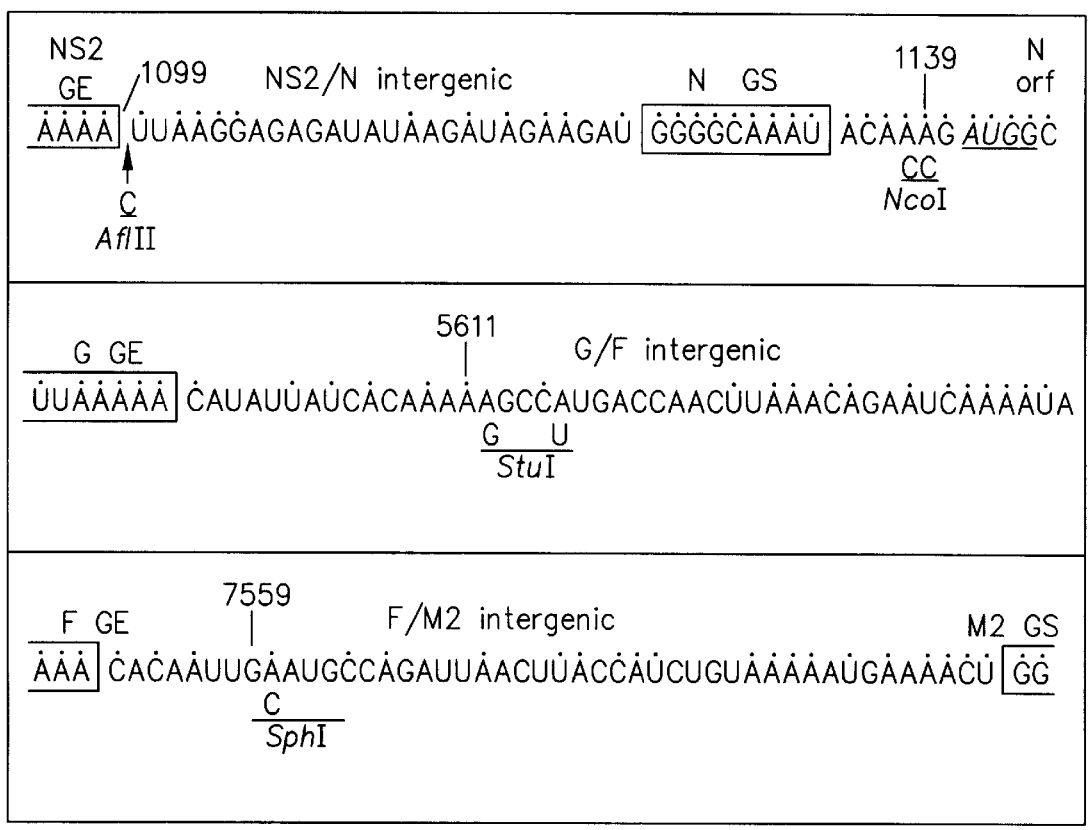

The sequence markers were inserted into the cDNA-encoded antigenome RNA as shown in FIG. 1B. Sequences are positive sense and numbered relative to the first nt of the leader region complement as 1; identities between strains A2 and 18537 (Johnson and Collins, *J. Gen Virol.* 69:2901–2906 (1988), incorporated herein by reference), representing subgroups A and B, respectively, are indicated with dots; sequences representing restriction sites in the cDNA are underlined; gene-start (GS) and gene-end (GE) transcription signals are boxed; the initiation codon of the N translational open reading frame at position 1141 is italicized, and the sequence markers are shown underneath each sequence. In the top sequence, a single C residue was inserted at position 1099 to create an AflII site in the NSII-N intergenic region, and the AG at positions 1139 and 1140 immediately upstream of the N translational open reading frame were replaced with CC to create a new NcoI site. In the middle sequence, substitution of G and U at positions 5612 and 5616, respectively, created a new StuI site in the G-F intergenic region. And, in the bottom sequence of FIG. 1B, a C replacement at position 7561 created a new SphI site in the F-M2 intergenic region.

All cDNAs were sequenced in their entirety, in most instances from several independent cDNAs, prior to assembly. The plasmids encoding individual RSV proteins are described in Grosfeld et al., *J. Virol.* 69:5677–5686 (1995) and Collins et al., *Proc. Natl. Acad. Sci. USA* (1995), each of which is incorporated herein by reference.

Example II

Transfection and Recovery of Recombinant RSV

The strategy for producing infectious RSV from cDNA-expressed antigenome involved its coexpression with those RSV proteins which are sufficient to (i) produce an antigenome nucleocapsid capable of RNA replication, and (ii) render the progeny genome nucleocapsid competent for both RNA replication and transcription. Transcription by the genome nucleocapsid provides all of the other RSV proteins and initiates a productive infection.

Plasmid-borne cDNA encoding the antigenome was transfected, together with plasmids encoding proteins N, P, L and M2(ORF1), into HEp-2 cells which had been infected with a recently-described vaccinia virus MVA strain recombinant which expresses the T7 RNA polymerase (Wyatt et al., *Virol.* 210:202–205 (1995), incorporated herein by reference). The MVA strain is a host range mutant which grows permissively in avian cells whereas in mammalian cells there is a block at a late stage in virion maturation that greatly reduces the production of infectious virus. In HEp-2 cells, the MVA recombinant was similar to the more commonly-used WR-based recombinant (Fuerst et al., *Proc. Natl. Acad. Sci. USA* 83: 8122–8126 (1986)) with regard to the level of expression of T7 polymerase and cytopathogenicity, but the level of progeny produced was sufficiently low that supernatants could be passaged to fresh cells with minimal cytopathogenicity. This should facilitate the recovery of any recombinant RSV which might be produced in transfected, vaccinia virus-infected cells.

Transfection and recovery of recombinant RSV was performed as follows. Monolayer cultures of HEp-2 cells received, per single well of a six-well dish, one ml of infection-transfection medium prepared by mixing five plasmids in a final volume of 0.1 ml Opti-MEM (Life Technologies) medium, namely 0.4 $\mu$g each of antigenome, N and P plasmids, and 0.1 $\mu$g each of L and M2(ORF1) plasmids. This was combined with 0.1 ml of Opti-MEM containing 12 $\mu$l LipofectACE (Life Technologies). After 15 min incubation at room temperature, this was combined with 0.8 ml of OptiMEM containing 2% heat-inactivated fetal calf serum and $1.5 \times 10^6$ pfu of strain MVA vaccinia virus recombinant encoding T7 RNA polymerase (Wyatt et al., supra). This was added to the cells and replaced one day later by Opti-MEM containing 2% serum. Cultures were incubated at 32° C. and harvested on day three. Incubation at 32° C. was used because it was found that the MVA virus is slightly temperature sensitive and is much more efficient at this lower temperature.

Three days post-transfection clarified culture supernatants were passaged onto fresh HEp-2 cells and overlaid with methyl cellulose (for subsequent antibody staining) or agarose (for plaque isolation). After incubation for five days under methyl cellulose, the cells were fixed and stained by an indirect horseradish peroxidase method using a mixture of three murine monoclonal antibodies to the RSV F protein followed by an anti-mouse antibody linked to horseradish peroxidase, following the general procedure of Murphy et al., *Vaccine* 8: 497–502 (1990).

Numerous RSV-like plaques were detected against a background of cytopathogenicity that presumably was due to a low level of MVA-T7 recombinant virus. The plaques contained an abundant amount of the RSV F protein, as indicated by brown-black coloration, and displayed cytopathic effects characteristic of RSV, notably syncytium formation.

The RSV-like plaques were picked from plates which had been prepared in parallel but incubated under agarose and stained with neutral red. They were propagated and compared to a laboratory strain of RSV strain A2 by plaque assay and antibody staining. The plaques derived from the transfected cultures closely resembled those of the laboratory strain. One difference was that the plaques derived from the transfected cultures appeared to be slightly smaller than those from the laboratory strain, with centers which were less well cleared. The recombinant virus may differ phenotypically from this particular wild type isolate, possibly being slightly more restricted in cell-to-cell spread and exhibiting a reduced rate of cell killing. With regard to the propagation of released virus, the yields of the recombinant versus laboratory virus in HEp-2 cells were essentially identical at 32° or 37° C. In preliminary studies, the recombinant and laboratory viruses were indistinguishable with regard to the accumulation of intracellular RSV mRNAs and proteins.

Plaque-purified, thrice-passaged recombinant RSV was analyzed in parallel with laboratory virus by RT-PCR using three primer pairs flanking the four inserted markers. Three independent plaque-purified recombinant RSV isolates were propagated in parallel with an uninfected control culture. Clarified medium supernatants were treated with polyethylene glycol and high salt (Zoller and Smith, *DNA* 3:479–488 (1984)) to precipitate virus and RNA was extracted from the pellets with Trizol™ (Life Technologies). These RNAs, in parallel with additional controls of no added RNA or 0.1 $\mu$g of RNA from a laboratory isolate of strain A2, were treated with DNAse, repurified, annealed each with 50 ng of random hexamers and incubated under standard RT conditions (40 $\mu$l reactions) with or without reverse transcriptase (Connors et al., *Virol.* 208: 478–484 (1995)). Aliquots of each reaction were subjected to PCR (35 cycles of 94° C. for 45s, 37° C. for 30s, 72° C. for 1 min) using three different pairs of synthetic deoxyoligonucleotide primers. Primer pair (A): positive-sense, positions 925–942 and negative-sense, positions 1421–1440, yielding a predicted product of 516 bp (517 bp in the case of the recombinant viruses) that included the AflII and NcoI sites inserted at, respectively, the junction of the NS2 and N genes and in the N gene. Primer pair (B): positive-sense, positions 5412–5429 and negative-sense, 5930–5949, yielding a predicted product of 538 bp spanning the StuI site inserted at the junction between the G and F genes. Primer pair (C): positive-sense, 7280–7297 and negative-sense, 7690–7707, yielding a 428 bp fragment spanning the SphI site inserted at the junction between the F and M2 genes. PCR products were analyzed by electrophoresis on neutral gels containing 1% agarose and 2% low-melting agarose in parallel with HaeIII-digested X174 DNA molecular length markers and visualized by staining with ethidium bromide. PCR products of the expected sizes were produced. The production of each was dependent on the RT step, indicating that each was derived from RNA rather than contaminating cDNA.

PCR products were analyzed by digestion with restriction enzymes. Digestion of products of primer pair A with AflII or NcoI yielded fragments corresponding to the predicted 177 and 340 bp (AflII) or 217 and 300 bp (NcoI). Digestion of products of primer pair B with StuI yielded fragments comparable to the predicted 201 and 337 bp. Digestion of products from reactions with primer pair C with SphI yielded products corresponding to the predicted 147 and 281 bp. The digests were analyzed by gel electrophoresis as above. The presence of residual undigested PCR product with AflII was due to incomplete digestion, as was confirmed by redigestion. Thus, the restriction enzyme digestion showed that the PCR products representing recombinant virus contained the expected restriction site markers while those representing the laboratory strain did not. Nucleotide sequence analysis of cloned PCR product confirmed the sequences spanning the restriction site markers.

As shown in Table 1, the efficiency of RSV production when complemented by N, P, L and M2(ORF1) was relatively high, ranging in three experiments from an average of 9.9 to 94.8 plaques per 0.4 μg of input antigenome cDNA and $1.5 \times 10^6$ cells. Since these plaques were derived from passage, the number of infected cells present in each well of the original transfection was not known. Nearly every transfected well (54 of 56 in Table 1) produced virus. Since the yield of released RSV per infected cell typically is very low (~10 pfu) even under ideal conditions, and since many wells yielded many times this amount (up to 169 plaques in Table 1), it is likely that several RSV producing cells were present in many of the wells of transfected cells.

RSV was not recovered if any of the plasmids were omitted (e.g., as shown in Table 1). The requirement for M2(ORF1) also could be satisfied with the complete gene, M2(ORF1+2), provided the level of its input cDNA was low (0.016 μg per $1.5 \times 10^6$ cells [Table 1]). At higher levels, the production of virus was greatly reduced, suggesting that an inhibition of minigenome RNA synthesis associated with M2(ORF2) also operates on the complete genome during productive infection.

These results showed that the production of infectious RSV was highly dependent on expression of the M2(ORF1) protein in addition to N, P and L. Furthermore, it showed that the optimal method of expression of M2(ORF1) was from an engineered cDNA in which ORF2 had been deleted, although the complete cDNA containing both ORFs also supported the production of RSV.

Thus, as part of the present invention, transcription by RSV differed from previously-described nonsegmented negative strand RNA viruses in requiring a fourth protein designated here as M2(ORF1), and previously called 22K or M2 (Collins et al., *J. Virol.* 54:65–71 (1985)). The M2(ORF1) protein was found to be an RNA polymerase elongation factor essential for processive, sequential transcription. This requirement provides the capability, as part of this invention, for introducing specific, predetermined changes into infectious RSV.

TABLE 1

Production of infectious RSV was dependent on expression of M2 ORF 1

| Complementing plasmids (μg cDNA per $1.5 \times 10^6$ cells and antigenome | Production of infectious RSV # plaques × # wells* | | |
|---|---|---|---|
| cDNA) 0.4 μg | expt. 1 | expt. 2 | expt. 3 |
| N(0.4) | | | |
| P(0.4) | 0 × 24 | 0 × 12 | 0 × 12 |
| L(0.1) | | | |
| N(0.4) | 0 × 19[§] | 0 × 4 | 9 × 1 |

TABLE 1-continued

Production of infectious RSV was dependent on expression of M2 ORF 1

| Complementing plasmids (μg cDNA per $1.5 \times 10^6$ cells and antigenome | Production of infectious RSV # plaques × # wells* | | |
|---|---|---|---|
| cDNA) 0.4 μg | expt. 1 | expt. 2 | expt. 3 |
| P(0.4) | 1 × 2 | 3 × 1 | 10 × 1 |
| L(0.1) | 2 × 2 | 5 × 1 | 14 × 2 |
| M2 [ORF1 + 2] (0.016) | 3 × 1 | 6 × 1 | 22 × 1 |
|  | av. 0.38 | 9 × 1 | 28 × 1 |
|  |  | 10 × 1 | 32 × 1 |
|  |  | 13 × 1 | 49 × 1 |
|  |  | 34 × 1 | 70 × 2 |
|  |  | 51 × 1 | 166 × 1 |
|  |  | av. 10.9 | 169 × 1 |
|  |  |  | av. 48.6 |
| N(0.4) | 0 × 1 | 11 × 1 | 0 × 1 | 55 × 1 |
| P(0.4) | 1 × 1 | 12 × 1 | 2 × 1 | 59 × 1 |
| L(0.1) | 2 × 2 | 13 × 1 | 4 × 1 | 65 × 1 |
| M2 [ORF1] (0.1) | 3 × 2 | 21 × 1 | 5 × 1 | 71 × 1 |
|  | 4 × 1 | 24 × 1 | 8 × 2 | 72 × 1 |
|  | 5 × 2 | 26 × 1 | 10 × 3 | 87 × 1 |
|  | 6 × 4 | 30 × 2 | 19 × 1 | 97 × 1 |
|  | 7 × 2 | 33 × 2 | 20 × 1 | 100 × 1 |
|  | 9 × 1 | 42 × 1 | 23 × 1 | 109 × 1 |
|  | 10 × 2 | 73 × 1 | av. 9.9 | 128 × 1 |
|  |  | av. 13.7 |  | 147 × 1 |
|  |  |  |  | 148 × 1 |
|  |  |  |  | av. 94.8 |

*Supernatants from transfected cultures ($10^6$ cells per well) were passaged onto fresh HEp-2 cells, overlaid with methyl cellulose, and stained with F-specific monoclonal antibodies.
[§]Read as follows: 19 wells had 0 plaques, 2 wells had 1 plaque each, 2 wells had 2 plaques each, and 1 well had 3 plaques.

Example III

Constructing Infectious RSV with Predetermined Mutations to Confer a Desired Phenotype This Example illustrates the introduction of specific predetermined mutations into infectious recombinant RSV using the methods described hereinabove. For ease of manipulation, the antigenome cDNA was cloned as two separate pieces in separate plasmids: one piece (the left end) containing the T7 promoter together with nucleotide 1 through to the BamHI site at nucleotide 8501 (cDNA D50), and the other (the right end) containing the BamHI site through to nucleotide 15223, together with the ribozyme and T7 transcription terminators (cDNA D39). D39 was further separated into two pieces and each placed in a separate phagemid plasmid: one piece (left hand half, cDNA L1) from the BamHI site to the PmlI site at nucleotide 12255, and the other (right hand half, cDNA L2) from the PmlI site to the end of the T7 terminator. The sequence positions assigned to restriction site locations are intended as a descriptive guide and do not alone precisely define all of the nucleotides involved.

Following a general procedure of Kunkel et al. *Meth. Enzymol.* 54:367–382 (1987) (incorporated herein by reference), the plasmids were propagated in a dut unq strain of *E. coli*, strain CJ236, and single stranded DNA was prepared by infection with a helper phage, M13KO7. Phosphorylated synthetic oligonucleotides each containing one or more nucleotide changes of interest were prepared, annealed to the single stranded template singly or more than one at a time, and used to direct DNA synthesis by T4 DNA polymerase. The products were ligated and transformed into a non-dut unq strain of *E. coli*, DH5α or DH10B. Colonies containing mutant plasmids were identified by restriction enzyme digestion or by sequence analysis. Other methods of mutagenesis can readily be used.

L1 and L2 described above were modified to contain several combinations of recognition sites for several different restriction enzymes which do not appear or are infrequent in the antigenome plasmid; these sites were introduced using nucleotide substitutions which did not change the amino acid sequence of the encoded L protein. In addition, L1 was modified to contain a mutation believed to confer a ts phenotype. Two versions of L1 were made. In one version, L1 was modified in a single cycle of mutagenesis to contain new Bsu36I (nucleotide 9399) and SnaBI (11848) sites, and a mutation termed 530, yielding cDNA 530L1sites. The 530 mutation had been identified by sequence analysis of the biologically-derived virus cpts530-RSV and involves a single nucleotide change at position 10060 which results in an amino acid change (Phe to Leu) at amino acid 521 in the L protein. In a second version, L1 was modified in a single cycle to contain the Bsu36I and SnaBI sites, resulting in cDNA L1 sites. L2 was modified in one cycle of mutagenesis to contain the new sites PmeI (13342), RsrII (14083) and SnaBI (14477). In a second cycle, the site BstEII (14318) was added and a naturally-occurring recognition site for SnaBI (6956) was removed. This yielded L2 sites.

Three complete antigenome cDNAs were made by introducing selected L1 and L2 mutant cDNAs or fragments thereof into D39 and combining this with D50. Antigenome cDNA "D53sites" contains L1 sites and L2 sites. cDNA "530D53" contains the BamHI-SpeI (10149) fragment of 530L1sites (which contains the Bsu36I and 530 mutations). cDNA "530D53sites" contained 530L1 sites and L2 sites (Table II). Recombinant virus was recovered from each of the three complete mutant antigenome cDNAs using the methodology of this invention and were passaged at least twice and analyzed directly or following plaque purification and amplification. The presence of mutations was confirmed by RT-PCR of viral RNA followed by analysis by restriction enzyme digestion or nucleotide sequencing, or both.

The engineered viruses were evaluated for their ability to form plaques in HEp-2 cells at 32° C., 39° C. and 40° C. in parallel with two nonrecombinant biologically-derived viruses, HEK, a wild type strain A2 virus, and cpts530 RSV, the virus from which the 530 mutation was identified by sequence analysis (Table II). This comparison showed that all three engineered viruses formed plaques at 32° C., and showed that the titers of the various virus preparations were within two $\log_{10}$ units of each other, which is within the range of experimental variation typically seen among independent preparations of RSV. The recombinant viruses containing the 530 mutation were greatly impaired in ability to form plaques at 39° C. or 40° C., comparable to cpts530 RSV. The presence of additional restriction sites in 530D53sites versus 530D53 had no discernable effect on the ts phenotype. D53sites virus, which contained silent restriction site markers but lacked the 530 mutation, retained the ability to form plaques at the higher temperatures, comparable to wild type. This not only provided positive identification that the 530 mutation is involved in the ts phenotype of cpts530 RSV, but also showed that point mutations can be introduced systematically into recombinant RSV according to the present invention. In these cases, the resulting phenotypes of the engineered viruses were fully consistent with the parental strain and provided direct confirmation and reconstitution of an attenuation mutation.

TABLE II

Characterization of the ts phenotype of biologically-derived RSV versus RSV recovered from cDNA clones

| virus | Efficiency of plaque formation ($\log_{10}$) at the indicated temperature | | |
|---|---|---|---|
| | 32° C. | 39° C. | 40° C. |
| Biologically-derived viruses | | | |
| HEK[a] | 8.7 | 8.6 | 8.5 |
| cpts530RSV[b] | 6.8 | <0.7 | <0.7 |
| cDNA-derived viruses | | | |
| D53 sites[c] | 6.9 | 6.9 | 6.7 |
| 530D53[d] | 7.9 | <0.7 | <0.7 |
| 530D53 sites[e] | 7.6 | <0.7 | <0.7 |

[a]Wild type RSV A2.
[b]ts virus.
[c]Contains six new restriction sites and lacks one naturally-occurring site.
[d]Contains one new restriction site and the 530 mutation.
[e]Contains six new restriction sites and the 530 mutation and lacks one naturally-occurring site.

Example IV

Recovery of Infectious Respiratory Syncytial Virus Expressing an Additional, Foreign Gene The methods described above were used to construct recombinant RSV containing an additional gene, encoding chloramphenicol acetyl transferase (CAT). The CAT coding sequence was flanked by RSV-specific gene-start and gene-end motifs, the transcription signals for the viral RNA-dependent RNA polymerase. The RSV/CAT chimeric transcription cassette was inserted into the intergenic region between the G and F genes of the complete cDNA-encoded positive-sense RSV antigenome, and infectious CAT-expressing recombinant RSV was recovered. The CAT mRNA was efficiently expressed and the levels of the G and F mRNAs were comparable to those expressed by wild type recombinant RSV. The CAT-containing and wild type viruses were similar with regard to the levels of synthesis of the major viral proteins.

Figure 2:
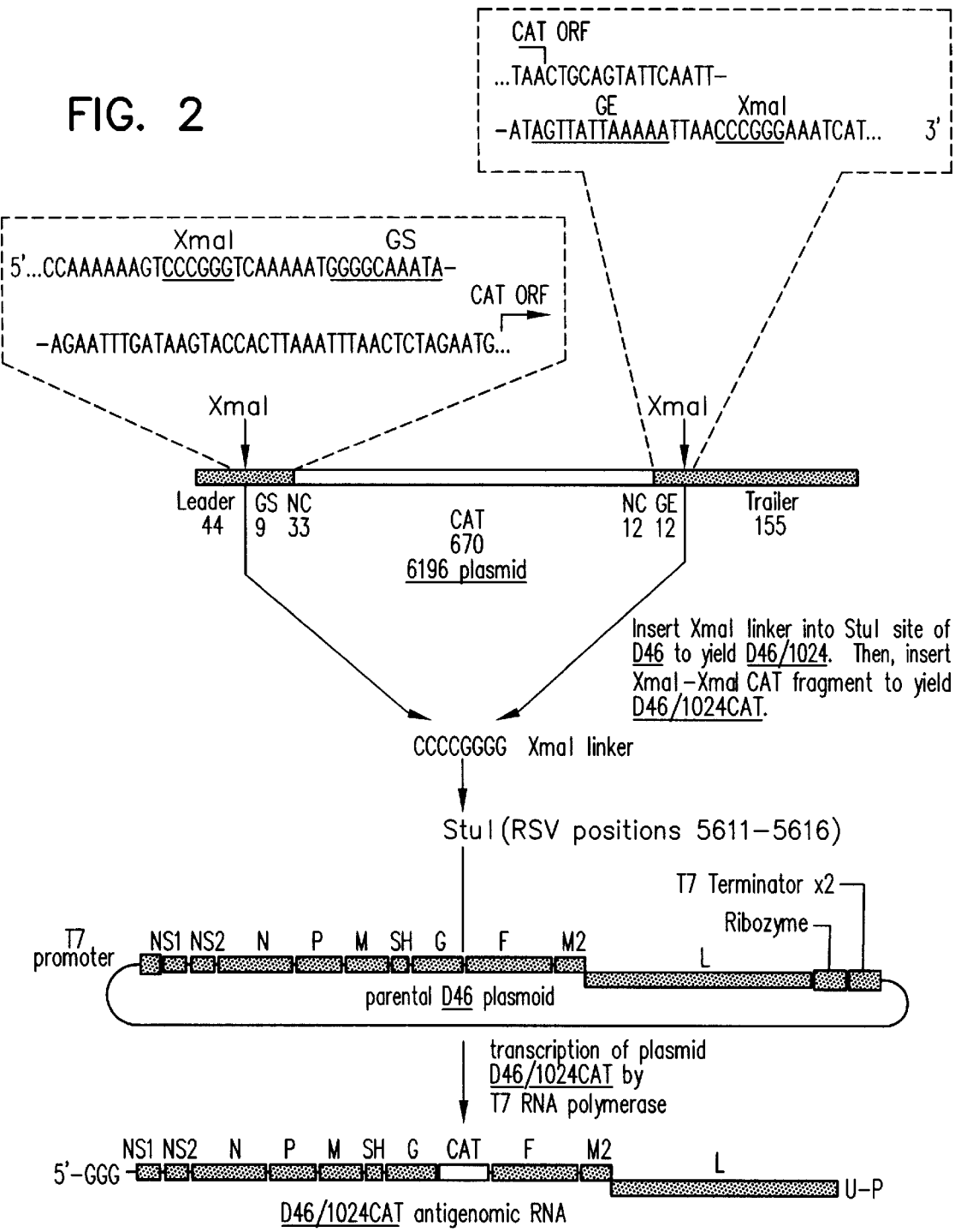
FIG. 2 shows construction of D46/1024CAT cDNA encoding an RSV antigenome containing the CAT ORF flanked by RSV transcription signals (not to scale, RSV-specific segments are shown as filled boxes and CAT sequence as an open box). The source of the CAT gene transcription cassette was RSV-CAT minigenome cDNA 6196 (diagram at top). The RSV-CAT minigenome contains the leader region, gene-start (GS) and gene-end (GE) signals, noncoding (NC) RSV gene sequences, and the CAT ORF, with XmaI restriction endonuclease sites preceding the GS signal and following the GE signal. The nucleotide lengths of these elements are indicated, and the sequences (positive-sense) surrounding the XmaI sites are shown above the diagram. A 8-nucleotide XmaI linker was inserted into StuI site of the parental plasmid D46 to construct the plasmid D46/1024. The XmaI—XmaI fragment of the plasmid 6196 was inserted into the plasmid D46/1024 to construct the plasmid D46/1024CAT. The RNA encoded by the D46 cDNA is shown at the bottom, including the three 5'-terminal nonviral G residues contributed by the T7 promoter and the 3'-terminal phosphorylated U residue contributed by cleavage of the hammerhead ribozyme; the nucleotide lengths do not include these nonviral nucleotides. The L gene is drawn offset to indicate the gene overlap.

Plasmid D46 was used for construction of cDNA encoding RSV antigenomic RNA containing the CAT gene. (Plasmids D46 and D50, the latter mentioned in Example III, are different preparations of the same antigenome cDNA.) D46 which encodes the complete, 15,223-nucleotide RSV antigenome (one nucleotide longer than that of wild type RSV) and was used to produce recombinant infectious RSV described above. During its construction, the antigenome cDNA had been modified to contain four new restriction sites as markers. One of these, a StuI site placed in the intergenic region between the G and F genes (positions 5611–5616 in the 3'-5' sequence of the wild type genome), was chosen as an insertion site for the foreign CAT gene. A copy of the CAT ORF flanked on the upstream end by the RSV GS signal and on the downstream end by the RS GE signal was derived from a previously-described RSV-CAT minigenome (Collins et al., *Proc. Natl. Acad. Sci. USA* 88:9663–9667 (1991) and Kuo et al., *J. Virol.* 70: 6892–6901 (1996), incorporated by reference herein). The insertion of this RSV/CAT transcription cassette into the StuI site, to yield the D46/1024CAT cDNA, increased the length of the encoded antigenome to a total of 15,984 nucleotides. And, whereas wild type RSV encodes ten major subgenomic mRNAs, the recombinant virus predicted from the D46/1024CAT antigenome would encode the CAT gene as an eleventh mRNA. The strategy of construction is shown in FIG. 2.

Producing infectious RSV from cDNA-encoded antigenomic RNA, as described above, involved coexpression in HEP-2 cells of five cDNAs separately encoding the antigenomic RNA or the N, P, L or M2(ORF1) protein, which are necessary and sufficient for viral RNA replication and transcription. cDNA expression was driven by T7 RNA polymerase supplied by a vaccinia-T7 recombinant virus based on the MVA strain. The MVA-T7 recombinant virus produced infectious progeny sufficient to cause extensive cytopathogenicity upon passage, and therefore, cytosine arabinoside, an inhibitor of vaccinia virus replication, was added 24 h following the transfection and maintained during the first six passages.

Two antigenome cDNAs were tested for the recovery of RSV: the D46 cDNA, and the D46/1024CAT cDNA. Each one yielded infectious recombinant RSV. Cells infected with the D46/1024CAT recombinant virus expressed abundant levels of CAT enzyme. For each virus, transfection supernatants were passaged to fresh cells, and a total of eight serial passages were performed at intervals of five to six days and a multiplicity of infection of less than 0.1 PFU per cell.

The CAT sequence in the D46/1024CAT genome was flanked by RSV GS and GE signals, and thus should be expressed as an additional, separate, polyadenylated mRNA. The presence of this predicted mRNA was tested by Northern blot hybridization of RNA from cells infected with D46/1024CAT virus or D46 virus at the eighth passage. Hybridization with a negative-sense CAT-specific riboprobe detected a major band which was of the appropriate size to be the predicted CAT mRNA, which would contain 735 nucleotides not including poly(A). This species was completely retained by oligo(dT) latex particles, showing that it was polyadenylated. In some cases, a minor larger CAT-specific species was detected which was of the appropriate size to be a G-CAT readthrough mRNA. The D46/1024CAT virus had been subjected to eight passages at low multiplicity of infection prior to the infection used for preparing the intracellular RNA. There was no evidence of shorter forms of the CAT mRNA, as might have arisen if the CAT gene was subject to deletion.

Replicate blots were hybridized with negative-sense riboprobe specific to the CAT, SH, G or F gene, the latter two genes flanking the inserted CAT gene. The blots showed that the expression of the subgenomic SH, G and F mRNAs was similar for the two viruses. Phosphoimagery was used to compare the amount of hybridized radioactivity in each of the three RSV mRNA bands for D46/1024CAT and D46. The ratio of radioactivity between D46/1024CAT and D46 was determined for each mRNA: SH, 0.77; G, 0.87; and F, 0.78. The deviation from unity probably indicates that slightly less RNA was loaded for D46/1024CAT versus D46, although it also is possible that the overall level of mRNA accumulation was slightly less for D46/1024CAT RSV. The demonstration that the three ratios were similar confirms that the level of expression of each of these mRNAs was approximately the same for D46/1024CAT versus D46. This, the insertion of the CAT gene between the G and F genes did not drastically affect the level of transcription of either gene.

To characterize viral protein synthesis, infected HEp-2 cells were labeled with [$^{35}$S]methionine, and cell lysates were analyzed by PAGE either directly or following immunoprecipitation under conditions where recovery of labeled antigen was essentially complete. Precipitation with a rabbit antiserum raised against purified RSV showed that the D46/1024CAT and D46 viruses both expressed similar amounts of the major viral proteins $F_1$, N, P, M, and M2. That a similar level of M2 protein was recovered for each virus was noteworthy because its gene is downstream of the inserted CAT gene. Accumulation of the F protein, which is encoded by the gene located immediately downstream of the insertion, also was examined by immunoprecipitation with a mixture of three anti-F monoclonal antibodies. A similar level of the $F_1$ subunit was recovered for each virus. Phosphorimagery analysis of the major viral proteins mentioned above was performed for several independent experiments and showed that some sample-to-sample variability, but overall the two viruses could not be distinguished on the basis of the level of recovered proteins. Precipitation with anti-CAT antibodies recovered a single species for the D46/1024CAT but not for the D46 virus. Analysis of the total labeled protein showed that the N, P and M proteins could be detected without immunoprecipitation (although detection of the latter was complicated by its comigration with a cellular species) and confirmed that the two viruses yielded similar patterns. The position corresponding to that of the CAT protein contained more radioactivity in the D46/1024CAT pattern compared to that of D46, as was confirmed by phosphorimagery of independent experiments. This suggested that the CAT protein could be detected among the total labeled proteins without precipitation, although this demonstration was complicated by the presence of a comigrating background band in the uninfected and D46-infected patterns.

RT-PCR was used to confirm the presence of the CAT gene in the predicted location of the genome of recombinant RSV. Total intracellular RNA was isolated from the cell pellet of passage eight of both D46/1024CAT and D46 RSV. Two primers were chosen that flank the site of insertion, the StuI restriction endonuclease site at RSV positions 5611–5616: the upstream positive-sense primer corresponded to positions 5412–5429, and the downstream negative-sense one to positions 5730–5711. The positive-sense primer was used for the RT step, and both primers were included in the PCR.

RT-PCR of the D46 virus yielded a single product that corresponded to the predicted fragment of 318 nucleotides, representing the G/F gene junction without additional foreign sequence. Analysis of D46/1024CAT viral RNA yielded a single product whose electrophoretic mobility corresponded well with the predicted 1079 nucleotide fragment, representing the G/F gene junction containing the inserted CAT transcription cassette. The latter PCR yielded a single major band; the absence of detectable smaller products indicated that the population of recombinant genomes did not contain a large number of molecules with a deletion in this region. When PCR analysis was performed on D46/1024CAT virus RNA without the RT step, no band was seen, confirming that the analysis was specific to RNA. Thus, the RT-PCR analysis confirmed the presence of an insert of the predicted length in the predicted location in the genomic RNA of the D46/1024CAT recombinant virus.

Enzyme expression was used to measure the stability of the CAT gene. Cell pellets from all of the passages beginning with the third were tested for CAT expression. For the virus D46/1024CAT, all these assays displayed conversion of [($^{14}$C] labeled chloramphenicol into acetylated forms. To investigate stability of expression, virus from 20 or 25 individual plaques from passage three or eight, respectively, was analyzed for CAT expression. All samples were positive, and the level of expression of CAT was similar for each of the 25 isolates from passage eight, as judged by assay of equivalent aliquots of cell lysate. This demonstrated that the activity of the CAT protein encoded by each isolate remained unimpaired by mutation.

To determine plaque morphology and size, beginning with the second passage, one-eighth of the medium supernatant (i.e., 0.5 ml) harvested from each passage stage was used to infect fresh HEp-2 cells in six-well plates that were incubated under methylcellulose overlay for five to seven days. The cells were then fixed and stained by incubation with monoclonal antibodies against RSV F protein followed by a second antibody linked to horseradish peroxidase. Earlier, it had been observed that recombinant RSV produced from cDNA D46 was indistinguishable from a naturally-occurring wild type RSV isolate with regard to efficiency of plaque formation over a range of temperatures in vitro, and the ability to replicate and cause disease when inoculated into the respiratory tract of previously uninfected chimpanzees. Thus, the D46 recombinant RSV was considered to be a virulent wild type strain. The plaques produced by the D46 and D46/1024CAT recombinant viruses were compared by antibody staining. Plaque morphology was very similar for the two viruses, although the average diameter of the CAT-containing recombinant plaques was 90 percent of that of the D46 virus, based on measurement of thirty randomly-selected plaques for each virus.

The efficiency of replication in tissue culture of the D46 and D46/1024CAT viruses was compared in a single step growth cycle. Triplicate monolayers of cells were infected with either virus, and samples were taken at 12 h intervals and quantitated by plaque assay. The results showed that the production of D46/1024CAT virus relative to D46 was delayed and achieved a maximum titer which was 20-fold lower.

These results show that it is possible to construct recombinant, helper-independent RSV expressing a foreign gene, in this instance the CAT gene. The recombinant RSV directed expression of the predicted polyadenylated subgenomic mRNA that encoded CAT protein, the protein being detected both by enzyme assay and by radioimmunoprecipitation. Other examples have produced RSV recombinants with the luciferase gene inserted at the same CAT site, or with the CAT or luciferase genes inserted between the SH and G genes. These viruses also exhibit reduced growth, whereas the numerous wild type recombinant viruses recovered exhibit undiminished growth. This indicates that the reduced growth indeed is associated with the inserted gene rather than being due to chance mutation elsewhere in the genome. The finding that insertion of a foreign gene into recombinant RSV reduced its level of replication and was stable during passage in vitro suggests that this provides yet another means for effecting attenuation for vaccine use. And, these results demonstrate that the methodology described herein is capable of recovering a virus that is restricted in growth.

These results also illustrate an advantage of the strategy of gene expression of the nonsegmented negative strand viruses, namely that the foreign coding sequences can be introduced as a separate transcription cassette that is expressed as a separate mRNA. The results also show that RSV can tolerate an increase of genome length of 762 nucleotides in the case of the CAT gene to a total of 15,984 nucleotides (1.05 times that of wild type RSV). The luciferase gene that was successfully recovered is almost three times longer.

The viral RNA-dependent RNA polymerases are known to have an error-prone nature due to the absence of proofreading and repair mechanisms. In RNA virus genomes, the frequency of mutation is estimated to be as high as $10^{-4}$–$10^{-5}$ per site on average (Holland et al., *Curr. Top. Microbiol. Immunol.* 176:1–20 (1992) and references therein). In the case of the recombinant D46/1024CAT RSV produced here, correct expression of the foreign gene would be irrelevant for virus replication and would be free to accumulate mutations. The passages described here involved a multiplicity of infection less than 0.1 PFU per cell, and the duration of each passage level indicated that multiple rounds of infection were involved. While yields of infectious virus from RSV-infected tissue culture cells typically are low, intracellular macromolecular synthesis is robust, and the poor yields of infectious virus seems to represent an inefficient step in packaging rather than low levels of RNA replication. Thus, the maintenance of CAT through eight serial passages involved many rounds of RNA replication. It was surprising that the nonessential CAT gene remained intact and capable of encoding fully functional protein in each of the 25 isolates tested at the eighth passage. Also, RT-PCR analysis of RNA isolated from passage eight did not detect deletions within the CAT gene.

Because most of the antigenic difference between the two RSV antigenic subgroups resides in the G glycoprotein, recombinant RSV can be constructed to express the G protein of the heterologous subgroup as an additional gene to yield a divalent vaccine. Envelope protein genes of some other respiratory viruses, such as human parainfluenza 3 virus, also can be inserted for expression by recombinant RSV. Other uses include coexpression of immune modulators such as interleukin 6 to enhance the immunogenicity of infectious RSV. Other uses, such as employing modified RSV as described herein as a vector for gene therapy, are also provided.

Although the foregoing invention has been described in some detail by way of illustration and example for purposes of clarity of understanding, it will be obvious that certain changes and modifications may be practiced within the scope of the appended claims.

What is claimed is:

1. An isolated infectious, self-replicating RSV particle which comprises a recombinant RSV genome or antigenome, a nucleocapsid (N) protein, a nucleocapsid phosphoprotein (P), a large (L) polymerase protein, and a M2(ORF1) RNA polymerase elongation factor.

2. The isolated infectious, self-replicating RSV particle of claim 1, which is a subviral particle.

3. The isolated infectious, self-replicating RSV particle of claim 1, which is a virus.

4. The isolated infectious, self-replicating RSV particle of claim 2, wherein the particle comprises a recombinant RSV antigenome.

5. The isolated infectious, self-replicating RSV particle of claim 1, wherein the particle comprises a recombinant RSV antigenome.

6. The isolated infectious, self-replicating RSV particle of claim 2, wherein the particle comprises a recombinant RSV genome.

7. The isolated infectious, self-replicating particle of claim 1, wherein the particle comprises a recombinant RSV genome.

8. The isolated infectious, self-replicating RSV virus of claim 1, which is a human RSV.

9. The isolated infectious, self-replicating RSV virus of claim 1, which is a bovine or murine RSV.

10. The isolated infectious, self-replicating RSV of claim 1, having a genome or antigenome that is a chimera of two or more different RSV genomes.

11. The isolated infectious, self-replicating RSV virus of claim 10, wherein the chimeric genome or antigenome comprises nucleotide sequences from human and bovine RSV.

12. A transfected, transformed, or transduced cell comprising one or more recombinant expression vector(s) that encode a RSV genome or antigenome and N, P, L and M2(ORF1) RNA polymerase elongation factor proteins of RSV.

13. The cell claim 12, wherein the RSV genome or antigenome and the N, P, L and M2(ORF1) RNA polymerase elongation factor proteins are encoded by a single expression vector.

14. The cell of claim 12, wherein multiple expression vectors encode the RSV genome or antigenome and the N, P, L and M2(ORF1) RNA polymerase elongation factor proteins.

15. The cell of claim 12, wherein the N, P, L and M2(ORF1) RNA polymerase elongation factor proteins are encoded by two or more expression vectors.

16. The cell of claim 15, wherein the N, P, L and M2(ORF1) RNA polymerase elongation factor proteins are each encoded by different expression vectors.

17. The cell of claim 12, whereby upon expression said RSV genome or antigenome and N, P, L, and RNA polymerase elongation factor proteins combine to produce an infectious RSV particle.

18. The cell of claim 12, wherein the RSV genome or antigenome is a human, bovine or murine RSV sequence.

19. A composition which comprises one or more isolated polynucleotide molecule(s) comprising at least one operably linked transcriptional promoter, at least one polynucleotide sequence that encode(s) an RSV genome or antigenome and N, P, L and M2(ORF1) RNA polymerase elongation factor proteins of RSV, and a transcriptional terminator.

20. The isolated polynucleotide molecule of claim 19, wherein the polynucleotide sequence encoding an RSV genome or antigenome is a human RSV sequence.

21. The isolated polynucleotide molecule of claim 20, wherein the polynucleotide sequence encoding a human RSV genome or antigenome is SEQ ID NO:1.

22. The isolated polynucleotide molecule of claim 19, wherein the polynucleotide sequence encoding an RSV genome or antigenome encodes a genome or antigenome of a nonhuman RSV or is a chimera of a nonhuman RSV and at least one other RSV of human or nonhuman origin.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 15223 base pairs
      (B) TYPE: nucleic acid (C) STRANDEDNESS: single
        (D) TOPOLOGY: linear (ii) MOLECULE TYPE: other (xi) SEQUENCE DESCRIPTION: SEQ ID NO:1:

```
ACGSGAAAAA ATGCGTACAA CAAACTTGCA TAAACCAAAA AAATGGGGCA AATAAGAATT      60

TGATAAGTAC CACTTAAATT TAACTCCCTT GGTTAGAGAT GGGCAGCAAT TCATTGAGTA     120

TGATAAAAGT TAGATTACAA AATTTGTTTG ACAATGATGA AGTAGCATTG TTAAAAATAA     180

CATGCTATAC TGATAAATTA ATACATTTAA CTAATGCTTT GGCTAAGGCA GTGATACATA     240

CAATCAAATT GAATGGCATT GTGTTTGTGC ATGTTATTAC AAGTAGTGAT ATTTGCCCTA     300

ATAATAATAT TGTAGTAAAA TCCAATTTCA CAACAATGCC AGTACTACAA AATGGAGGTT     360

ATATATGGGA AATGATGGAA TTAACACATT GCTCTCAACC TAATGGTCTA CTAGATGACA     420

ATTGTGAAAT TAAATTCTCC AAAAAACTAA GTGATTCAAC AATGACCAAT TATATGAATC     480

AATTATCTGA ATTACTTGGA TTTGATCTTA ATCCATAAAT TATAATTAAT ATCAACTAGC     540

AAATCAATGT CACTAACACC ATTAGTTAAT ATAAAACTTA ACAGAAGACA AAAATGGGGC     600

AAATAAATCA ATTCAGCCAA CCCAACCATG GACACAACCC ACAATGATAA TACACCACAA     660

AGACTGATGA TCACAGACAT GAGACCGTTG TCACTTGAGA CCATAATAAC ATCACTAACC     720

AGAGACATCA TAACACACAA ATTTATATAC TTGATAAATC ATGAATGCAT AGTGAGAAAA     780

CTTGATGAAA AGCAGGCCAC ATTTACATTC CTGGTCAACT ATGAAATGAA ACTATTACAC     840

AAAGTAGGAA GCACTAAATA TAAAAAATAT ACTGAATACA ACACAAAATA TGGCACTTTC     900

CCTATGCCAA TATTCATCAA TCATGATGGG TTCTTAGAAT GCATTGGCAT TAAGCCTACA     960

AAGCATACTC CCATAATATA CAAGTATGAT CTCAATCCAT AAATTTCAAC ACAATATTCA    1020

CACAATCTAA AACAACAACT CTATGCATAA CTATACTCCA TAGTCCAGAT GGAGCCTGAA    1080

AATTATAGTA ATTTAAAACT TAAGGAGAGA TATAAGATAG AAGATGGGGC AAATACAACC    1140

ATGGCTCTTA GCAAAGTCAA GTTGAATGAT ACACTCAACA AAGATCAACT TCTGTCATCC    1200

AGCAAATACA CCATCCAACG GAGCACAGGA GATAGTATTG ATACTCCTAA TTATGATGTG    1260

CAGAAACACA TCAATAAGTT ATGTGGCATG TTATTAATCA CAGAAGATGC TAATCATAAA    1320

TTCACTGGGT TAATAGGTAT GTTATATGCG ATGTCTAGGT TAGGAAGAGA AGACACCATA    1380

AAAATACTCA GAGATGCGGG ATATCATGTA AAAGCAAATG GAGTAGATGT AACAACACAT    1440

CGTCAAGACA TTAATGGAAA AGAAATGAAA TTTGAAGTGT TAACATTGGC AAGCTTAACA    1500

ACTGAAATTC AAATCAACAT TGAGATAGAA TCTAGAAAAT CCTACAAAAA AATGCTAAAA    1560

GAAATGGGAG AGGTAGCTCC AGAATACAGG CATGACTCTC CTGATTGTGG GATGATAATA    1620

TTATGTATAG CAGCATTAGT AATAACTAAA TTAGCAGCAG GGACAGATC TGGTCTTACA    1680

GCCGTGATTA GGAGAGCTAA TAATGTCCTA AAAAATGAAA TGAAACGTTA CAAAGGCTTA    1740

CTACCCAAGG ACATAGCCAA CAGCTTCTAT GAAGTGTTTG AAAAACATCC CCACTTTATA    1800

GATGTTTTTG TTCATTTTGG TATAGCACAA TCTTCTACCA GAGGTGGCAG TAGAGTTGAA    1860

GGGATTTTTG CAGGATTGTT TATGAATGCC TATGGTGCAG GGCAAGTGAT GTTACGGTGG    1920

GGAGTCTTAG CAAAATCAGT TAAAAATATT ATGTTAGGAC ATGCTAGTGT CAAGCAGAA    1980

ATGGAACAAG TTGTTGAGGT TTATGAATAT GCCCAAAAAT TGGGTGGTGA AGCAGGATTC    2040

TACCATATAT TGAACAACCC AAAAGCATCA TTATTATCTT TGACTCAATT TCCTCACTTC    2100

TCCAGTGTAG TATTAGGCAA TGCTGCTGGC CTAGGCATAA TGGGAGAGTA CAGAGGTACA    2160
```

-continued

```
CCGAGGAATC AAGATCTATA TGATGCAGCA AAGGCATATG CTGAACAACT CAAAGAAAAT    2220

GGTGTGATTA ACTACAGTGT ACTAGACTTG ACAGCAGAAG AACTAGAGGC TATCAAACAT    2280

CAGCTTAATC CAAAAGATAA TGATGTAGAG CTTTGAGTTA ATAAAAAATG GGCAAATAA     2340

ATCATCATGG AAAAGTTTGC TCCTGAATTC CATGGAGAAG ATGCAAACAA CAGGGCTACT    2400

AAATTCCTAG AATCAATAAA GGGCAAATTC ACATCACCCA AAGATCCCAA GAAAAAAGAT    2460

AGTATCATAT CTGTCAACTC AATAGATATA GAAGTAACCA AGAAAGCCC TATAACATCA     2520

AATTCAACTA TTATCAACCC AACAAATGAG ACAGATGATA CTGCAGGGAA CAAGCCCAAT    2580

TATCAAAGAA AACCTCTAGT AAGTTTCAAA GAAGACCCTA CACCAAGTGA TAATCCCTTT    2640

TCTAAACTAT ACAAGAAAC CATAGAAACA TTTGATAACA ATGAAGAAGA ATCCAGCTAT     2700

TCATACGAAG AAATAAATGA TCAGACAAAC GATAATATAA CAGCAAGATT AGATAGGATT    2760

GATGAAAAAT TAAGTGAAAT ACTAGGAATG CTTCACACAT TAGTAGTGGC AAGTGCAGGA    2820

CCTACATCTG CTCGGGATGG TATAAGAGAT GCCATGGTTG GTTAAGAGA AGAAATGATA     2880

GAAAAAATCA GAACTGAAGC ATTAATGACC AATGACAGAT TAGAAGCTAT GGCAAGACTC    2940

AGGAATGAGG AAAGTGAAAA GATGGCAAAA GACACATCAG ATGAAGTGTC TCTCAATCCA    3000

ACATCAGAGA AATTGAACAA CCTATTGGAA GGGAATGATA GTGACAATGA TCTATCACTT    3060

GAAGATTTCT GATTAGTTAC CAATCTTCAC ATCAACACAC AATACCAACA GAAGACCAAC    3120

AAACTAACCA ACCCAATCAT CCAACCAAAC ATCCATCCGC CAATCAGCCA ACAGCCAAC     3180

AAAACAACCA GCCAATCCAA AACTAACCAC CCGGAAAAAA TCTATAATAT AGTTACAAAA    3240

AAAGGAAAGG GTGGGGCAAA TATGGAAACA TACGTGAACA AGCTTCACGA AGGCTCCACA    3300

TACACAGCTG CTGTTCAATA CAATGTCTTA GAAAAAGACG ATGACCCTGC ATCACTTACA    3360

ATATGGGTGC CCATGTTCCA ATCATCTATG CCAGCAGATT TACTTATAAA GAACTAGCT    3420

AATGTCAACA TACTAGTGAA ACAAATATCC ACACCCAAGG GACCTTCACT AAGAGTCATG    3480

ATAAACTCAA GAAGTGCAGT GCTAGCACAA ATGCCCAGCA AATTTACCAT ATGCGCTAAT    3540

GTGTCCTTGG ATGAAAGAAG CAAACTAGCA TATGATGTAA CCACACCCTG TGAAATCAAG    3600

GCATGTAGTC TAACATGCCT AAAATCAAAA AATATGTTGA CTACAGTTAA AGATCTCACT    3660

ATGAAGACAC TCAACCCTAC ACATGATATT ATTGCTTTAT GTGAATTTGA AAACATAGTA    3720

ACATCAAAAA AAGTCATAAT ACCAACATAC CTAAGATCCA TCAGTGTCAG AAATAAAGAT    3780

CTGAACACAC TTGAAAATAT AACAACCACT GAATTCAAAA ATGCTATCAC AAATGCAAAA    3840

ATCATCCCTT ACTCAGGATT ACTATTAGTC ATCACAGTGA CTGACAACAA AGGAGCATTC    3900

AAATACATAA AGCCACAAAG TCAATTCATA GTAGATCTTG GAGCTTACCT AGAAAAAGAA    3960

AGTATATATT ATGTTACCAC AAATTGGAAG CACACAGCTA CACGATTTGC AATCAAACCC    4020

ATGGAAGATT AACCTTTTTC CTCTACATCA GTGTGTTAAT TCATACAAAC TTTCTACCTA    4080

CATTCTTCAC TTCACCATCA CAATCACAAA CACTCTGTGG TTCAACCAAT CAAACAAAAC    4140

TTATCTGAAG TCCAGATCA TCCCAAGTCA TTGTTTATCA GATCTAGTAC TCAAATAAGT     4200

TAATAAAAAA TATACACATG GGGCAAATAA TCATTGGAGG AAATCCAACT AATCACAATA    4260

TCTGTTAACA TAGACAAGTC CACACACCAT ACAGAATCAA CCAATGGAAA ATACATCCAT    4320

AACAATAGAA TTCTCAAGCA AATTCTGGCC TTACTTTACA CTAATACACA TGATCACAAC    4380

AATAATCTCT TTGCTAATCA TAATCTCCAT CATGATTGCA ATACTAAACA AACTTTGTGA    4440

ATATAACGTA TTCCATAACA AAACCTTTGA GTTACCAAGA GCTCGAGTCA ACACATAGCA    4500

TTCATCAATC CAACAGCCCA AAACAGTAAC CTTGCATTTA AAAATGAACA ACCCCTACCT    4560
```

-continued

```
CTTTACAACA CCTCATTAAC ATCCCACCAT GCAAACCACT ATCCATACTA TAAAGTAGTT   4620

AATTAAAAAT AGTCATAACA ATGAACTAGG ATATCAAGAC TAACAATAAC ATTGGGGCAA   4680

ATGCAAACAT GTCCAAAAAC AAGGACCAAC GCACCGCTAA GACATTAGAA AGGACCTGGG   4740

ACACTCTCAA TCATTTATTA TTCATATCAT CGTGCTTATA TAAGTTAAAT CTTAAATCTG   4800

TAGCACAAAT CACATTATCC ATTCTGGCAA TGATAATCTC AACTTCACTT ATAATTGCAG   4860

CCATCATATT CATAGCCTCG GCAAACCACA AAGTCACACC AACAACTGCA ATCATACAAG   4920

ATGCAACAAG CCAGATCAAG AACACAACCC CAACATACCT CACCCAGAAT CCTCAGCTTG   4980

GAATCAGTCC CTCTAATCCG TCTGAAATTA CATCACAAAT CACCACCATA CTAGCTTCAA   5040

CAACACCAGG AGTCAAGTCA ACCCTGCAAT CCACAACAGT CAAGACCAAA ACACAACAA    5100

CAACTCAAAC ACAACCCAGC AAGCCCACCA CAAAACAACG CCAAAACAAA CCACCAAGCA   5160

AACCCAATAA TGATTTTCAC TTTGAAGTGT TCAACTTTGT ACCCTGCAGC ATATGCAGCA   5220

ACAATCCAAC CTGCTGGGCT ATCTGCAAAA GAATACCAAA CAAAAAACCA GGAAAGAAAA   5280

CCACTACCAA GCCCACAAAA AAACCAACCC TCAAGACAAC CAAAAAAGAT CCCAAACCTC   5340

AAACCACTAA ATCAAAGGAA GTACCCACCA CCAAGCCCAC AGAAGAGCCA ACCATCAACA   5400

CCACCAAAAC AAACATCATA ACTACACTAC TCACCTCCAA CACCACAGGA ATCCAGAAC    5460

TCACAAGTCA AATGGAAACC TTCCACTCAA CTTCCTCCGA AGGCAATCCA AGCCCTTCTC   5520

AAGTCTCTAC AACATCCGAG TACCCATCAC AACCTTCATC TCCACCCAAC ACACCACGCC   5580

AGTAGTTACT TAAAAACATA TTATCACAAA AGGCCTTGAC CAACTTAAAC AGAATCAAAA   5640

TAAACTCTGG GGCAAATAAC AATGGAGTTG CTAATCCTCA AAGCAAATGC AATTACCACA   5700

ATCCTCACTG CAGTCACATT TTGTTTTGCT TCTGGTCAAA ACATCACTGA AGAATTTTAT   5760

CAATCAACAT GCAGTGCAGT TAGCAAAGGC TATCTTAGTG CTCTGAGAAC TGGTTGGTAT   5820

ACCAGTGTTA TAACTATAGA ATTAAGTAAT ATCAAGAAAA ATAAGTGTAA TGGAACAGAT   5880

GCTAAGGTAA AATTGATAAA ACAAGAATTA GATAAATATA AAAATGCTGT AACAGAATTG   5940

CAGTTGCTCA TGCAAAGCAC ACAAGCAACA AACAATCGAG CCAGAAGAGA ACTACCAAGG   6000

TTTATGAATT ATACACTCAA CAATGCCAAA AAACCAATG TAACATTAAG CAAGAAAAGG    6060

AAAAGAAGAT TTCTTGGTTT TTTGTTAGGT GTTGGATCTG CAATCGCCAG TGGCGTTGCT   6120

GTATCTAAGG TCCTGCACCT AGAAGGGGAA GTGAACAAGA TCAAAAGTGC TCTACTATCC   6180

ACAAACAAGG CTGTAGTCAG CTTATCAAAT GGAGTTAGTG TTTTAACCAG CAAAGTGTTA   6240

GACCTCAAAA ACTATATAGA TAAACAATTG TTACCTATTG TGAACAAGCA AAGCTGCAGC   6300

ATATCAAATA TAGAAACTGT GATAGAGTTC CAACAAAAGA ACAACAGACT ACTAGAGATT   6360

ACCAGGGAAT TTAGTGTTAA TGCAGGCGTA ACTACACCTG TAAGCACTTA CATGTTAACT   6420

AATAGTGAAT TATTGTCATT AATCAATGAT ATGCCTATAA CAAATGATCA GAAAAGTTA    6480

ATGTCCAACA ATGTTCAAAT AGTTAGACAG CAAAGTTACT CTATCATGTC CATAATAAAA   6540

GAGGAAGTCT TAGCATATGT AGTACAATTA CCACTATATG GTGTTATAGA TACACCCTGT   6600

TGGAAACTAC ACACATCCCC TCTATGTACA ACCAACACAA AAGAAGGGTC CAACATCTGT   6660

TTAACAAGAA CTGACAGAGG ATGGTACTGT GACAATGCAG GATCAGTATC TTTCTTCCCA   6720

CAAGCTGAAA CATGTAAAGT TCAATCAAAT CGAGTATTTT GTGACACAAT GAACAGTTTA   6780

ACATTACCAA GTGAAGTAAA TCTCTGCAAT GTTGACATAT TCAACCCCAA ATATGATTGT   6840

AAAATTATGA CTTCAAAAAC AGATGTAAGC AGCTCCGTTA TCACATCTCT AGGAGCCATT   6900

GTGTCATGCT ATGGCAAAAC TAAATGTACA GCATCCAATA AAAATCGTGG AATCATAAAG   6960
```

```
ACATTTTCTA ACGGGTGCGA TTATGTATCA AATAAAGGGG TGGACACTGT GTCTGTAGGT      7020

AACACATTAT ATTATGTAAA TAAGCAAGAA GGTAAAAGTC TCTATGTAAA AGGTGAACCA      7080

ATAATAAATT TCTATGACCC ATTAGTATTC CCCTCTGATG AATTTGATGC ATCAATATCT      7140

CAAGTCAACG AGAAGATTAA CCAGAGCCTA GCATTTATTC GTAAATCCGA TGAATTATTA      7200

CATAATGTAA ATGCTGGTAA ATCCACCACA AATATCATGA TAACTACTAT AATTATAGTG      7260

ATTATAGTAA TATTGTTATC ATTAATTGCT GTTGGACTGC TCTTATACTG TAAGGCCAGA      7320

AGCACACCAG TCACACTAAG CAAAGATCAA CTGAGTGGTA TAAATAATAT TGCATTTAGT      7380

AACTAAATAA AAATAGCACC TAATCATGTT CTTACAATGG TTTACTATCT GCTCATAGAC      7440

AACCCATCTG TCATTGGATT TTCTTAAAAT CTGAACTTCA TCGAAACTCT CATCTATAAA      7500

CCATCTCACT TACACTATTT AAGTAGATTC CTAGTTTATA GTTATATAAA ACACAATTGC      7560

ATGCCAGATT AACTTACCAT CTGTAAAAAT GAAAACTGGG GCAAATATGT CACGAAGGAA      7620

TCCTTGCAAA TTTGAAATTC GAGGTCATTG CTTAAATGGT AAGAGGTGTC ATTTTAGTCA      7680

TAATTATTTT GAATGGCCAC CCCATGCACT GCTTGTAAGA CAAAACTTTA TGTTAAACAG      7740

AATACTTAAG TCTATGGATA AAAGTATAGA TACCTTATCA GAAATAAGTG GAGCTGCAGA      7800

GTTGGACAGA ACAGAAGAGT ATGCTCTTGG TGTAGTTGGA GTGCTAGAGA GTTATATAGG      7860

ATCAATAAAC AATATAACTA AACAATCAGC ATGTGTTGCC ATGAGCAAAC TCCTCACTGA      7920

ACTCAATAGT GATGATATCA AAAAGCTGAG GGACAATGAA GAGCTAAATT CACCCAAGAT      7980

AAGAGTGTAC AATACTGTCA TATCATATAT TGAAAGCAAC AGGAAAAACA ATAAACAAAC      8040

TATCCATCTG TTAAAAAGAT TGCCAGCAGA CGTATTGAAG AAAACCATCA AAACACATT      8100

GGATATCCAT AAGAGCATAA CCATCAACAA CCCAAAAGAA TCAACTGTTA GTGATACAAA      8160

TGACCATGCC AAAAATAATG ATACTACCTG ACAAATATCC TTGTAGTATA ACTTCCATAC      8220

TAATAACAAG TAGATGTAGA GTTACTATGT ATAATCAAAA GAACACACTA TATTTCAATC      8280

AAAACAACCC AAATAACCAT ATGTACTCAC CGAATCAAAC ATTCAATGAA ATCCATTGGA      8340

CCTCTCAAGA ATTGATTGAC ACAATTCAAA ATTTTCTACA ACATCTAGGT ATTATTGAGG      8400

ATATATATAC AATATATATA TTAGTGTCAT AACACTCAAT TCTAACACTC ACCACATCGT      8460

TACATTATTA ATTCAAACAA TTCAAGTTGT GGGACAAAAT GGATCCCATT ATTAATGGAA      8520

ATTCTGCTAA TGTTTATCTA ACCGATAGTT ATTTAAAAGG TGTTATCTCT TTCTCAGAGT      8580

GTAATGCTTT AGGAAGTTAC ATATTCAATG GTCCTTATCT CAAAAATGAT TATACCAACT      8640

TAATTAGTAG ACAAAATCCA TTAATAGAAC ACATGAATCT AAAGAAACTA AATATAACAC      8700

AGTCCTTAAT ATCTAAGTAT CATAAAGGTG AAATAAAATT AGAAGAACCT ACTTATTTTC      8760

AGTCATTACT TATGACATAC AAGAGTATGA CCTCGTCAGA ACAGATTGCT ACCACTAATT      8820

TACTTAAAAA GATAATAAGA AGAGCTATAG AAATAAGTGA TGTCAAAGTC TATGCTATAT      8880

TGAATAAACT AGGGCTTAAA GAAAAGGACA AGATTAAATC CAACAATGGA CAAGATGAAG      8940

ACAACTCAGT TATTACGACC ATAATCAAAG ATGATATACT TTCAGCTGTT AAAGATAATC      9000

AATCTCATCT TAAAGCAGAC AAAAATCACT CTACAAAACA AAAAGACACA ATCAAAACAA      9060

CACTCTTGAA GAAATTGATG TGTTCAATGC AACATCCTCC ATCATGGTTA ATACATTGGT      9120

TTAACTTATA CACAAAATTA AACAACATAT TAACACAGTA TCGATCAAAT GAGGTAAAAA      9180

ACCATGGGTT TACATTGATA GATAATCAAA CTCTTAGTGG ATTTCAATTT ATTTTGAACC      9240

AATATGGTTG TATAGTTTAT CATAAGGAAC TCAAAAGAAT TACTGTGACA ACCTATAATC      9300

AATTCTTGAC ATGGAAAGAT ATTAGCCTTA GTAGATTAAA TGTTTGTTTA ATTACATGGA      9360
```

```
TTAGTAACTG CTTGAACACA TTAAATAAAA GCTTAGGCTT AAGATGCGGA TTCAATAATG    9420

TTATCTTGAC ACAACTATTC CTTTATGGAG ATTGTATACT AAAGCTATTT CACAATGAGG    9480

GGTTCTACAT AATAAAAGAG GTAGAGGGAT TTATTATGTC TCTAATTTTA AATATAACAG    9540

AAGAAGATCA ATTCAGAAAA CGATTTTATA ATAGTATGCT CAACAACATC ACAGATGCTG    9600

CTAATAAAGC TCAGAAAAAT CTGCTATCAA GAGTATGTCA TACATTATTA GATAAGACAG    9660

TGTCCGATAA TATAATAAAT GGCAGATGGA TAATTCTATT AAGTAAGTTC CTTAAATTAA    9720

TTAAGCTTGC AGGTGACAAT AACCTTAACA ATCTGAGTGA ACTATATTTT TTGTTCAGAA    9780

TATTTGGACA CCCAATGGTA GATGAAAGAC AAGCCATGGA TGCTGTTAAA ATTAATTGCA    9840

ATGAGACCAA ATTTTACTTG TTAAGCAGTC TGAGTATGTT AAGAGGTGCC TTTATATATA    9900

GAATTATAAA AGGGTTTGTA AATAATTACA ACAGATGGCC TACTTTAAGA AATGCTATTG    9960

TTTTACCCTT AAGATGGTTA ACTTACTATA AACTAAACAC TTATCCTTCT TTGTTGGAAC   10020

TTACAGAAAG AGATTTGATT GTGTTATCAG GACTACGTTT CTATCGTGAG TTTCGGTTGC   10080

CTAAAAAAGT GGATCTTGAA ATGATTATAA ATGATAAAGC TATATCACCT CCTAAAAATT   10140

TGATATGGAC TAGTTTCCCT AGAAATTACA TGCCATCACA CATACAAAAC TATATAGAAC   10200

ATGAAAAATT AAAATTTTCC GAGAGTGATA AATCAAGAAG AGTATTAGAG TATTATTTAA   10260

GAGATAACAA ATTCAATGAA TGTGATTTAT ACAACTGTGT AGTTAATCAA AGTTATCTCA   10320

ACAACCCTAA TCATGTGGTA TCATTGACAG GCAAAGAAAG AGAACTCAGT GTAGGTAGAA   10380

TGTTTGCAAT GCAACCGGGA ATGTTCAGAC AGGTTCAAAT ATTGGCAGAG AAAATGATAG   10440

CTGAAAACAT TTTACAATTC TTTCCTGAAA GTCTTACAAG ATATGGTGAT CTAGAACTAC   10500

AAAAAATATT AGAACTGAAA GCAGGAATAA GTAACAAATC AAATCGCTAC AATGATAATT   10560

ACAACAATTA CATTAGTAAG TGCTCTATCA TCACAGATCT CAGCAAATTC AATCAAGCAT   10620

TTCGATATGA AACGTCATGT ATTTGTAGTG ATGTGCTGGA TGAACTGCAT GGTGTACAAT   10680

CTCTATTTTC CTGGTTACAT TTAACTATTC CTCATGTCAC AATAATATGC ACATATAGGC   10740

ATGCACCCCC CTATATAGGA GATCATATTG TAGATCTTAA CAATGTAGAT GAACAAAGTG   10800

GATTATATAG ATATCACATG GGTGGCATCG AAGGGTGGTG TCAAAAACTA TGGACCATAG   10860

AAGCTATATC ACTATTGGAT CTAATATCTC TCAAAGGGAA ATTCTCAATT ACTGCTTTAA   10920

TTAATGGTGA CAATCAATCA ATAGATATAA GCAAACCAAT CAGACTCATG GAAGGTCAAA   10980

CTCATGCTCA AGCAGATTAT TTGCTAGCAT TAAATAGCCT TAAATTACTG TATAAAGAGT   11040

ATGCAGGCAT AGGCCACAAA TTAAAAGGAA CTGAGACTTA TATATCACGA GATATGCAAT   11100

TTATGAGTAA AACAATTCAA CATAACGGTG TATATTACCC AGCTAGTATA AAGAAAGTCC   11160

TAAGAGTGGG ACCGTGGATA AACACTATAC TTGATGATTT CAAAGTGAGT CTAGAATCTA   11220

TAGGTAGTTT GACACAAGAA TTAGAATATA GAGGTGAAAG TCTATTATGC AGTTTAATAT   11280

TTAGAAATGT ATGGTTATAT AATCAGATTG CTCTACAATT AAAAAATCAT GCATTATGTA   11340

ACAATAAACT ATATTTGGAC ATATTAAAGG TTCTGAAACA CTTAAAAACC TTTTTTAATC   11400

TTGATAATAT TGATACAGCA TTAACATTGT ATATGAATTT ACCCATGTTA TTTGGTGGTG   11460

GTGATCCCAA CTTGTTATAT CGAAGTTTCT ATAGAAGAAC TCCTGACTTC CTCACAGAGG   11520

CTATAGTTCA CTCTGTGTTC ATACTTAGTT ATTATACAAA CCATGACTTA AAAGATAAAC   11580

TTCAAGATCT GTCAGATGAT AGATTGAATA AGTTCTTAAC ATGCATAATC ACGTTTGACA   11640

AAAACCCTAA TGCTGAATTC GTAACATTGA TGAGAGATCC TCAAGCTTTA GGGTCTGAGA   11700

GACAAGCTAA AATTACTAGC GAAATCAATA GACTGGCAGT TACAGAGGTT TTGAGTACAG   11760
```

-continued

```
CTCCAAACAA AATATTCTCC AAAAGTGCAC AACATTATAC TACTACAGAG ATAGATCTAA    11820

ATGATATTAT GCAAAATATA GAACCTACAT ATCCTCATGG GCTAAGAGTT GTTTATGAAA    11880

GTTTACCCTT TTATAAAGCA GAGAAAATAG TAAATCTTAT ATCAGGTACA AAATCTATAA    11940

CTAACATACT GGAAAAAACT TCTGCCATAG ACTTAACAGA TATTGATAGA GCCACTGAGA    12000

TGATGAGGAA AAACATAACT TTGCTTATAA GGATACTTCC ATTGGATTGT AACAGAGATA    12060

AAAGAGAGAT ATTGAGTATG GAAAACCTAA GTATTACTGA ATTAAGCAAA TATGTTAGGG    12120

AAAGATCTTG GTCTTTATCC AATATAGTTG GTGTTACATC ACCCAGTATC ATGTATACAA    12180

TGGACATCAA ATATACTACA AGCACTATAT CTAGTGGCAT AATTATAGAG AAATATAATG    12240

TTAACAGTTT AACACGTGGT GAGAGAGGAC CCACTAAACC ATGGGTTGGT TCATCTACAC    12300

AAGAGAAAAA AACAATGCCA GTTTATAATA GACAAGTCTT AACCAAAAAA CAGAGAGATC    12360

AAATAGATCT ATTAGCAAAA TTGGATTGGG TGTATGCATC TATAGATAAC AAGGATGAAT    12420

TCATGGAAGA ACTCAGCATA GGAACCCTTG GGTTAACATA TGAAAAGGCC AAGAAATTAT    12480

TTCCACAATA TTTAAGTGTC AATTATTTGC ATCGCCTTAC AGTCAGTAGT AGACCATGTG    12540

AATTCCCTGC ATCAATACCA GCTTATAGAA CAACAAATTA TCACTTTGAC ACTAGCCCTA    12600

TTAATCGCAT ATTAACAGAA AAGTATGGTG ATGAAGATAT TGACATAGTA TTCCAAAACT    12660

GTATAAGCTT TGGCCTTAGT TTAATGTCAG TAGTAGAACA ATTTACTAAT GTATGTCCTA    12720

ACAGAATTAT TCTCATACCT AAGCTTAATG AGATACATTT GATGAAACCT CCCATATTCA    12780

CAGGTGATGT TGATATTCAC AAGTTAAAAC AAGTGATACA AAAACAGCAT ATGTTTTTAC    12840

CAGACAAAAT AAGTTTGACT CAATATGTGG AATTATTCTT AAGTAATAAA ACACTCAAAT    12900

CTGGATCTCA TGTTAATTCT AATTTAATAT TGGCACATAA AATATCTGAC TATTTTCATA    12960

ATACTTACAT TTTAAGTACT AATTTAGCTG GACATTGGAT TCTGATTATA CAACTTATGA    13020

AAGATTCTAA AGGTATTTTT GAAAAAGATT GGGGAGAGGG ATATATAACT GATCATATGT    13080

TTATTAATTT GAAAGTTTTC TTCAATGCTT ATAAGACCTA TCTCTTGTGT TTTCATAAAG    13140

GTTATGGCAA AGCAAAGCTG GAGTGTGATA TGAACACTTC AGATCTTCTA TGTGTATTGG    13200

AATTAATAGA CAGTAGTTAT TGGAAGTCTA TGTCTAAGGT ATTTTTAGAA CAAAAAGTTA    13260

TCAAATACAT TCTTAGCCAA GATGCAAGTT TACATAGAGT AAAAGGATGT CATAGCTTCA    13320

AATTATGGTT TCTTAAACGT CTTAATGTAG CAGAATTCAC AGTTTGCCCT TGGGTTGTTA    13380

ACATAGATTA TCATCCAACA CATATGAAAG CAATATTAAC TTATATAGAT CTTGTTAGAA    13440

TGGGATTGAT AAATATAGAT AGAATACACA TTAAAAATAA ACACAAATTC AATGATGAAT    13500

TTTATACTTC TAATCTCTTC TACATTAATT ATAACTTCTC AGATAATACT CATCTATTAA    13560

CTAAACATAT AAGGATTGCT AATTCTGAAT TAGAAAATAA TTACAACAAA TTATATCATC    13620

CTACACCAGA AACCCTAGAG AATATACTAG CCAATCCGAT TAAAAGTAAT GACAAAAAGA    13680

CACTGAATGA CTATTGTATA GGTAAAAATG TTGACTCAAT AATGTTACCA TTGTTATCTA    13740

ATAAGAAGCT TATTAAATCG TCTGCAATGA TTAGAACCAA TTACAGCAAA CAAGATTTGT    13800

ATAATTTATT CCCTATGGTT GTGATTGATA GAATTATAGA TCATTCAGGC AATACAGCCA    13860

AATCCAACCA ACTTTACACT ACTACTTCCC ACCAAATATC CTTAGTGCAC AATAGCACAT    13920

CACTTTACTG CATGCTTCCT TGGCATCATA TTAATAGATT CAATTTTGTA TTTAGTTCTA    13980

CAGGTTGTAA AATTAGTATA GAGTATATTT TAAAAGATCT TAAAATTAAA GATCCCAATT    14040

GTATAGCATT CATAGGTGAA GGAGCAGGGA ATTTATTATT GCGTACAGTA GTGGAACTTC    14100

ATCCTGACAT AAGATATATT TACAGAAGTC TGAAAGATTG CAATGATCAT AGTTTACCTA    14160
```

```
-continued

TTGAGTTTTT AAGGCTGTAC AATGGACATA TCAACATTGA TTATGGTGAA AATTTGACCA    14220

TTCCTGCTAC AGATGCAACC AACAACATTC ATTGGTCTTA TTTACATATA AAGTTTGCTG    14280

AACCTATCAG TCTTTTTGTC TGTGATGCCG AATTGTCTGT AACAGTCAAC TGGAGTAAAA    14340

TTATAATAGA ATGGAGCAAG CATGTAAGAA AGTGCAAGTA CTGTTCCTCA GTTAATAAAT    14400

GTATGTTAAT AGTAAAATAT CATGCTCAAG ATGATATTGA TTTCAAATTA GACAATATAA    14460

CTATATTAAA AACTTATGTA TGCTTAGGCA GTAAGTTAAA GGGATCGGAG GTTTACTTAG    14520

TCCTTACAAT AGGTCCTGCG AATATATTCC CAGTATTTAA TGTAGTACAA AATGCTAAAT    14580

TGATACTATC AAGAACCAAA AATTTCATCA TGCCTAAGAA AGCTGATAAA GAGTCTATTG    14640

ATGCAAATAT TAAAAGTTTG ATACCCTTTC TTTGTTACCC TATAACAAAA AAAGGAATTA    14700

ATACTGCATT GTCAAAACTA AAGAGTGTTG TTAGTGGAGA TATACTATCA TATTCTATAG    14760

CTGGACGTAA TGAAGTTTTC AGCAATAAAC TTATAAATCA TAAGCATATG AACATCTTAA    14820

AATGGTTCAA TCATGTTTTA AATTTCAGAT CAACAGAACT AAACTATAAC CATTTATATA    14880

TGGTAGAATC TACATATCCT TACCTAAGTG AATTGTTAAA CAGCTTGACA ACCAATGAAC    14940

TTAAAAAACT GATTAAAATC ACAGGTAGTC TGTTATACAA CTTTCATAAT GAATAATGAA    15000

TAAAGATCTT ATAATAAAAA TTCCCATAGC TATACACTAA CACTGTATTC AATTATAGTT    15060

ATTAAAAATT AAAAATCATA TAATTTTTTA AATAACTTTT AGTGAACTAA TCCTAAAGTT    15120

ATCATTTTAA TCTTGGAGGA ATAAATTTAA ACCCTAATCT AATTGGTTTA TATGTGTATT    15180

AACTAAATTA CGAGATATTA GTTTTTGACA CTTTTTTTCT CGT                      15223
```